United States Patent
Ramesh et al.

(10) Patent No.: US 6,635,446 B1
(45) Date of Patent: Oct. 21, 2003

(54) WIP, A WASP-ASSOCIATED PROTEIN

(75) Inventors: Narayanaswamy Ramesh, Wayland, MA (US); Ines M. Anton, Brookline, MA (US); John H. Hartwig, Jamaica Plain, MA (US); Raif S. Geha, Belmont, MA (US)

(73) Assignee: The Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/599,287

(22) Filed: Jun. 22, 2000

Related U.S. Application Data

(63) Continuation of application No. PCT/US98/27501, filed on Dec. 22, 1998.
(60) Provisional application No. 60/101,457, filed on Sep. 23, 1998, and provisional application No. 60/068,533, filed on Dec. 23, 1997.

(51) Int. Cl.⁷ ............................ C12P 21/06; C12N 5/00; C12N 1/20; C12N 15/00; C07H 21/04; C07K 17/00
(52) U.S. Cl. ................... 435/69.1; 435/325; 435/252.3; 435/320.1; 536/23.5; 530/395
(58) Field of Search ............................... 536/23.1, 23.4, 536/23.5; 435/69.1, 455, 320.1, 252.3, 325; 530/395

(56) References Cited

FOREIGN PATENT DOCUMENTS

| | | |
|---|---|---|
| GB | 2 311 783 A | 8/1997 |
| WO | WO 99/32628 | 7/1999 |

OTHER PUBLICATIONS

Attwood TK. Genomics. The Babel of bioinformatics. Science. 290(5491):471–473, 2000.*

Skolnick et al. From genes to protein structure and function: novel applications of computational approaches in the genomic era. Trends Biotechnol. 18(1):34–9, 2000.*

Meinkoth J, Wahl G. Hybridization of nucleic acids immobilized on solid supports. Anal Biochem. 1984 May 1;138(2):267–84.*

Ngo J.T, Marks J., Karplus M., Computational complexity, protein structure prediction, and the Levinthal paradox in The Protein Folding Problem, ch. 14, pp. 435–508, Birkhauser, 1994.*

Antón, I.M., et al., "WIP Deficiency Reveals a Differential Role for WIP and the Actin Cytoskeleton in T and B Cell Activation," *Immunity*, 16:1–20 (2002).

GenBank Accession No. AA501229, dbEST Id: 1145859, Clone Id: IMAGE: 891622 (5') 1997.

GenBank Accession No. B65694, dbGSS Id: 65846, Clone Id: 2022M15 1998.

Zhang, J., et al., "Antigen Receptor–induced Activation and Cytoskeletal Rearrangement Are Impaired in Wiskott–Aldrich Syndrome Protein–deficient Lymphocytes," *J. Exp. Med.*, 190(9):1329–1341 (1999).

Savoy, D.N., et al., "Cutting Edge: WPI, a Binding Partner for Wiskott–Aldrich Syndrome Protein, Cooperates with Vav in the Regulation of T Cell Activation," *J. of Immunology* 164:2866–2870 (2000).

Martinez–Quiles, N., et al., "WIP regulates N–WASP–mediated actin polymerization and filopodium formation," *Nature Cell Biology* 3(5):484–491 (2001).

Snapper, S.B., et al., "Wiskott–Aldrich Syndrome Protein–Deficient Mice Reveal a Role for WASP in T but Not B Cell Activation," *Immunity* 9:81–91 (1998).

Ramesh, N. et al., "Identification of a novel protein that interacts with Wiskott–Aldrich syndrome protein (WASP)", Poster presented at AAAA/AAI/CIS Joint Meeting, Apr. 1997.

Kreideweiss, S. et al., "*H.sapiens* mRNA for PRPL–2 protein", GenBank Accesssion No.: X86019, Locus: HSPRPL2 (Jan. 6, 1998).

Ramesh, N. et al., "Identification of a novel protein that interacts with Wiskott–Aldrich syndrome protein (WASP).", *Journal of Allergy and Clinical Immunology* vol. 99, No. 1, Part 2, Supp. S!, 727 (1997); Joint meeting of the American Academy of Allergy, Asthma and Immunology, The American Association of Immunologists and The Clinic Immunology Society San Francisco, California, US Feb. 21–26, 1997; Abstract No. 727.

Ruhlmann, A. et al., "Gene from: *H.sapiens* mRNA for PRPL–2 protein", GenBank Accession No.: 762950, Locus: 762950 (Apr. 4, 1995).

(List continued on next page.)

*Primary Examiner*—Christina Chan
*Assistant Examiner*—Maher Haddad
(74) *Attorney, Agent, or Firm*—Hamilton, Brook, Smith & Reynolds, P.C.

(57) ABSTRACT

Described herein is a novel gene and its product, WIP, which associates with WASP. The subject invention relates to the isolated WIP gene or cDNA (see FIGS. 1A–1B); nucleic acid probes, which can be fragments of the WIP gene or WIP cDNA or full-length; nucleic acid primers, which are fragments of WIP cDNA or the WIP gene; methods of assessing cells (e.g., for diagnostic purposes) for the presence of WIP DNA, (e.g., wildtype or mutated) or for the absence or occurrence of a reduced level of WIP DNA; WIP mRNA; WIP or WIP fragments, such as those which are useful to generate antibodies which bind WIP; and antibodies which bind WIP. Also the subject of this invention are methods of treating conditions in which WIP and/or WASP DNA or protein is deficient (in quantity) and/or defective (e.g., mutated/altered) such that an individual is adversely affected (e.g., has Wiskott-Aldrich Syndrome); methods of altering or regulating WASP and its functions; and methods of altering actin content, actin polymerization or both in cells, such as human lymphoid cells (e.g., β lymphocytes). A further subject of this invention is an assay to identify drugs which alter (e.g., enhance) the activity of WIP or expression of WIP DNA.

23 Claims, 7 Drawing Sheets

OTHER PUBLICATIONS

Ruhlmann, A. et al., "*H.sapiens* mRNA for PRPL–2 protein", GenBank Accession No.:X86019, Locus HSPRPL2, (Apr. 4, 1995).

Ruhlmann, A. et al., "prpL_2 gene product", GenBank Accession No.: 762951, Locus: 762951 (Apr. 4, 1995).

Stewart, D.M. et al., "*Homo sapiens* Wiskott–Aldrich syndrome protein interacting protein (WASPIP) mRNA, partial cds.", GenBank Accession No.: AF106062, Locus: AF106062 (Jul. 31, 1999).

Antón, I.M. et al., "The Wiskott–Aldrich Syndrome Protein–interacting Protein (WIP) Binds to the Adaptor Protein Nck", *J. Biol. Chem.*273 (33):20992–20995 (1998).

Banin, S. et al., "Wiskott–Aldrich syndrome protein (WASp) is a binding partner for c–Src family protein–tyrosiine kinases", *Curr. Biol.* 6(8):981–988 (1996).

Cooper, M.D. et al., "Wiskott–Aldrich Syndrome: An Immunologic Deficiency Disease Involving the Afferent Limb of Immunity", *Am. J. Med.* 44:499–513 (1968).

Donnelly, S. F. H. et al., "A proline–rich protein, verprolin, involved in cytoskeletal organization and cellular growth in the yeast *Saccharomyces cerevisiae*", *Mol. Microbiol.* 10(3):585–596 (1993).

Featherstone, C., "The Many Faces of WAS Protein", *Science* 275:27–28 (1997).

Gertler, F. B. et al., "Mena, a Relative of VASP and Drosophila Enabled, Is Implicated in the Control of Microfilament Dynamics", *Cell* 87(2):227–239 (1996).

Kolluri, R. et al., "Direct interaction of the Wiskott–Aldrich syndrome protein with the GTPase Cdc42", *Proc. Natl. Acad. Sci. USA* 93:5615–5618 (1996).

Lehmann, J. M. et al., "Nck, a melanoma cDNA encoding a cytoplasmic protein consisting of the src homology units SH2 and SH3", *Nucleic Acids Research* 18(4):1048 (1990).

Meisenhelder, J. and T. Hunter, "The SH2/SH3 Domain–Containing Protein Nck Is Recognized by Certain Anti–Phospholipase C–γ1 Monoclonal Antibodies, An Its Phosphorylation on Tyrosine Is Stimulated by Platelet–Derived Growth Factor and Epidermal Growth Factor Treatment", *Molecular and Cellular Biology* 12(12):5843–5856 (1992).

Prasad, K. V. et al., "Src–homology 3 domain of protein kinase p59$^{fyn}$ mediates binding to phosphatidylinositol 3–kinase in T cells", *Proc. Natl. Acad. Sci. USA* 90:7366–7370 (1993).

Purich, D. L. and F. S. Southwick, "ABM–1 and ABM–2 Homology Sequences: Consensus Docking Sites for Actin–Based Motility Defined by Oligoproline Regions in Listeria ActA Surface Protein and Human VASP", *Biochem. and Biophys. Res. Commun.* 231:686–691 (1997).

Ramesh, N. et al., "WIP, a protein associated with Wiskott–Aldrich syndrome protein, induces actin polymerization and redistribution in lymphoid cells", *Proc. Natl. Acad. Sci. USA* 94:14671–14676 (1997).

Reinhard, M. et al., "The proline–rich focal adhesion and microfilament protein VASP is a ligand for profilins", *The EMBO Journal* 14(8):1583–1589 (1995).

Rivero–Lezcano, O. M. et al., "Wiskott–Aldrich Syndrome Protein Physically Associates with Nck through Src Homology 3 Domains", *Mol. Cell. Biol.* 15(10):5725–5731 (1995).

Stewart, D. M. et al., "Mutations That Cause the Wiskott–Aldrich Syndrome Impair the Interaction of Wiskkott–Aldrich Syndrome Protein (WASP) with WASP Interacting Protein", *J. Immunol.* 162:5019–5024 (1999).

Symons, M. et al., "Wiskott–Aldrich Syndrome Protein, a Novel Effector for the GTPase CDC43Hs, Is Implicated in Actin Polymerization", *Cell* 84(5):723–734 (1996).

Theriot, J. A. and T.J. Mitchison, "The Three Faces of Profilin", *Cell* 75(5):835–838 (1993).

Troys, M. V. et al., "The actin binding site of thymosin β4 mapped by mutational analysis", *The EMBO Journal* 15(2):201–210 (1996).

Vaduva, G. et al., "The Human WASP–interacting Protein, WIP, Activates the Cell Polarity Pathway in Yeast", *J. Biol. Chem.* 274(24):17103–17108 (1999).

Vaduva, G. et al., "Wiskott–Aldrich Syndrome Protein interacting protein, WIP, complements verprolin function in yeast cells", Poster presented at the 14th Annual Symposium in Cellular Endocrinology; Cellular Signaling & the Cytoskeleton, Sep. 1998.

Antón, I.M. et al., "The Wiskott–Aldrich Syndrome Protein–Interacting Protein (WIP) Binds to the Adaptor Protein Nck and Induces Actin Clusters After PDGF Stimulation", Poster presented a the 14th Annual Symposium in Cellular Endocrinology; Cellular Signaling & the Cytoskeleton, Sep. 1998.

\* cited by examiner

| | | | | | | | | | | | | | | | | |
|---|---|---|---|---|---|---|---|---|---|---|---|---|---|---|---|---|
| ccc | ggg | cag | gtt | aga | aga | cag | cag | ggg | aac | tcg | aga | agt | tgg | ttg | ttt | 48 |
| Pro | Gly | Gln | Val | Arg | Arg | Gln | Gln | Gly | Asn | Ser | Arg | Ser | Trp | Leu | Phe | |
| 1 | | | | 5 | | | | | 10 | | | | | 15 | | |
| tca | gca | gat | taa | aac | aat | aca | gat | tta | tca | gca | aga | ctg | ttc | aac | gca | 96 |
| Ser | Ala | Asp | OCH | Asn | Asn | Thr | Asp | Leu | Ser | Ala | Arg | Leu | Phe | Asn | Ala | |
| | | | | 20 | | | | | 25 | | | | | 30 | | |
| taa | ctg | ccc | aag | atg | cct | gtc | cct | ccc | cct | cca | gca | ccc | ccg | ccg | ccc | 144 |
| OCH | Leu | Pro | Lys | Met | Pro | Val | Pro | Pro | Pro | Pro | Ala | Pro | Pro | Pro | Pro | |
| | | | | 35 | | | | | 40 | | | | | 45 | | |
| ccg | acg | ttt | gca | ctg | gcc | aat | aca | gag | aag | cct | acc | ttg | aat | aag | aca | 192 |
| Pro | Thr | Phe | Ala | Leu | Ala | Asn | Thr | Glu | Lys | Pro | Thr | Leu | Asn | Lys | Thr | |
| | | | | 50 | | | | | 55 | | | | | 60 | | |
| gag | cag | gct | ggg | aga | aat | gct | ctc | ctt | tct | gat | atc | agc | aaa | ggg | aag | 240 |
| Glu | Gln | Ala | Gly | Arg | Asn | Ala | Leu | Leu | Ser | Asp | Ile | Ser | Lys | Gly | Lys | |
| | | | | 65 | | | | | 70 | | | | | 75 | | |
| aaa | cta | aag | aag | acg | gtc | acc | aat | gac | aga | agt | gca | cca | ata | ctg | gac | 288 |
| Lys | Leu | Lys | Lys | Thr | Val | Thr | Asn | Asp | Arg | Ser | Ala | Pro | Ile | Leu | Asp | |
| | | | | 80 | | | | | 85 | | | | | 90 | | |
| aaa | cct | aaa | gga | gct | ggt | gct | gga | ggc | ggt | ggt | ggt | ggc | ttt | ggt | gga | 336 |
| Lys | Pro | Lys | Gly | Ala | Gly | Ala | Gly | Gly | Gly | Gly | Gly | Gly | Phe | Gly | Gly | |
| 95 | | | | | 100 | | | | | 105 | | | | | 110 | |
| ggc | ggc | gga | ttt | ggc | gga | gga | ggt | ggt | ggc | gga | ggc | ggt | gga | aGT | TTT | 384 |
| Gly | Gly | Gly | Phe | Gly | Gly | Gly | Gly | Gly | Gly | Gly | Gly | Gly | Gly | Ser | Phe | |
| | | | | 115 | | | | | 120 | | | | | 125 | | |
| GGA | GGG | GGC | GGA | CCT | CCA | GGT | CTG | GGA | GGA | TTG | TTC | CAG | GCT | GGA | ATG | 432 |
| Gly | Gly | Gly | Gly | Pro | Pro | Gly | Leu | Gly | Gly | Leu | Phe | Gln | Ala | Gly | Met | |
| | | | | 130 | | | | | 135 | | | | | 140 | | |
| CCG | AAG | CTG | AGA | TCC | ACC | GCC | AAC | AGG | GAT | AAT | GAT | TCT | GGA | GGA | AGC | 480 |
| Pro | Lys | Leu | Arg | Ser | Thr | Ala | Asn | Arg | Asp | Asn | Asp | Ser | Gly | Gly | Ser | |
| | | | | 145 | | | | | 150 | | | | | 155 | | |
| CGA | CCA | CCA | TTG | TTG | CCA | CCG | GGA | GGA | AGA | TCC | ACA | TCT | GCG | AAA | CCC | 528 |
| Arg | Pro | Pro | Leu | Leu | Pro | Pro | Gly | Gly | Arg | Ser | Thr | Ser | Ala | Lys | Pro | |
| | | | | 160 | | | | | 165 | | | | | 170 | | |
| TTT | TCA | CCC | CCA | AGT | GGC | CCA | GGG | AGG | TTT | CCT | GTG | CCT | TCT | CCA | GGC | 576 |
| Phe | Ser | Pro | Pro | Ser | Gly | Pro | Gly | Arg | Phe | Pro | Val | Pro | Ser | Pro | Gly | |
| 175 | | | | | 180 | | | | | 185 | | | | | 190 | |
| CAC | AGA | AGT | GGT | CCC | CCA | GAG | CCT | CAG | AGG | AAC | CGA | ATG | CCG | CCC | CCA | 624 |
| His | Arg | Ser | Gly | Pro | Pro | Glu | Pro | Gln | Arg | Asn | Arg | Met | Pro | Pro | Pro | |
| | | | | 195 | | | | | 200 | | | | | 205 | | |
| AGG | CCC | GAC | GTG | GGC | TCA | AAG | CCT | GAT | AGC | ATT | CCT | CCT | CCA | GTA | CCT | 672 |
| Arg | Pro | Asp | Val | Gly | Ser | Lys | Pro | Asp | Ser | Ile | Pro | Pro | Pro | Val | Pro | |
| | | | | 210 | | | | | 215 | | | | | 220 | | |
| AGT | ACT | CCA | AGA | CCC | ATT | CAA | TCA | AGT | CTG | CAC | AAC | CGG | GGG | TCC | CCA | 720 |
| Ser | Thr | Pro | Arg | Pro | Ile | Gln | Ser | Ser | Leu | His | Asn | Arg | Gly | Ser | Pro | |
| | | | | 225 | | | | | 230 | | | | | 235 | | |
| CCA | GTG | CCC | GGA | GGC | CCC | AGG | CAG | CCC | AGC | CCC | GGG | CCC | ACT | CCT | CCC | 768 |
| Pro | Val | Pro | Gly | Gly | Pro | Arg | Gln | Pro | Ser | Pro | Gly | Pro | Thr | Pro | Pro | |
| | | | | 240 | | | | | 245 | | | | | 250 | | |
| CCT | TTC | CCT | GGA | AAC | CGC | GGC | ACT | GCT | TTG | GGA | GGA | GGC | TCA | ATA | CGT | 816 |
| Pro | Phe | Pro | Gly | Asn | Arg | Gly | Thr | Ala | Leu | Gly | Gly | Gly | Ser | Ile | Arg | |
| 255 | | | | | 260 | | | | | 265 | | | | | 270 | |
| CAG | TCC | CCC | TTG | AGC | TCC | TCC | TCG | CCC | TTC | TCC | AAC | CGG | CCT | CCC | CTC | 864 |
| Gln | Ser | Pro | Leu | Ser | Ser | Ser | Ser | Pro | Phe | Ser | Asn | Arg | Pro | Pro | Leu | |
| | | | | 275 | | | | | 280 | | | | | 285 | | |
| CCG | CCT | ACC | CCC | AGC | AGG | GCG | TTG | GAT | GAC | AAA | CCC | CCT | CCA | CCA | CCT | 912 |
| Pro | Pro | Thr | Pro | Ser | Arg | Ala | Leu | Asp | Asp | Lys | Pro | Pro | Pro | Pro | Pro | |
| | | | | 290 | | | | | 295 | | | | | 300 | | |

FIG. 1A

```
CCT CCA GTG GGC AAC AGG CCC TCC ATC CAC AGG GAA GCG GTT CCC CCT      960
Pro Pro Val Gly Asn Arg Pro Ser Ile His Arg Glu Ala Val Pro Pro
        305                 310                 315
CCT CCT CCT CAG AAC AAC AAG CCT CCA GTG CCT TCC ACT CCG CGG CCT     1008
Pro Pro Pro Gln Asn Asn Lys Pro Pro Val Pro Ser Thr Pro Arg Pro
        320                 325                 330
TCG GCT CCT CAC AGG CCC CAC CTC CGC CCG CCA CCT CCC AGC AGG CCC     1056
Ser Ala Pro His Arg Pro His Leu Arg Pro Pro Pro Pro Ser Arg Pro
335                 340                 345                 350
GGG CCG CCT CCT CTG CCT CCA AGT TCC AGC GGC AAT GAC GAA ACC CCA     1104
Gly Pro Pro Pro Leu Pro Pro Ser Ser Ser Gly Asn Asp Glu Thr Pro
                355                 360                 365
AGA CTC CCA CAG CGG AAT CTG TCC CTC AGT TCG TCC ACG CCC CCG TTA     1152
Arg Leu Pro Gln Arg Asn Leu Ser Leu Ser Ser Thr Pro Pro Leu
                370                 375                 380
CCT TCG CCA GGA CGT TCA GGT CCT CTT CCT CCC CCA GTG CCC AGT GAG     1200
Pro Ser Pro Gly Arg Ser Gly Pro Leu Pro Pro Pro Val Pro Ser Glu
        385                 390                 395
AGA CCC CCA CCT CCA GTG AGG GAC CCG CCA GGC CGA TCA GGC CCC CTC     1248
Arg Pro Pro Pro Pro Val Arg Asp Pro Pro Gly Arg Ser Gly Pro Leu
        400                 405                 410
CCA CCA CCT CCT CCA GTA AGC AGA AAC GGC AGC ACA TCT CGG GCC CTG     1296
Pro Pro Pro Pro Pro Val Ser Arg Asn Gly Ser Thr Ser Arg Ala Leu
415                 420                 425                 430
CCT GCT ACC CCT CAG TTG CCA TCC AGG AGT GGA GTA GAC AGT CCC AGG     1344
Pro Ala Thr Pro Gln Leu Pro Ser Arg Ser Gly Val Asp Ser Pro Arg
                435                 440                 445
AGT GGA CCC AGG CCT CCC CTT CCT CCT GAT AGG CCC AGT GCT GGG GCA     1392
Ser Gly Pro Arg Pro Pro Leu Pro Pro Asp Arg Pro Ser Ala Gly Ala
                450                 455                 460
CCT CCC CCA CCT CCA CCA TCA ACA TCT ATT AGA AAT GGC TTC CAA GAC     1440
Pro Pro Pro Pro Pro Pro Ser Thr Ser Ile Arg Asn Gly Phe Gln Asp
        465                 470                 475
TCT CCA TGT GAA GAT GAG TGG GAA AGC AGA TTC TAC TTC CAT CCG ATT     1488
Ser Pro Cys Glu Asp Glu Trp Glu Ser Arg Phe Tyr Phe His Pro Ile
        480                 485                 490
TCC GAT TTG CCA CCT CCA GAG CCA TAT GTA CAA ACG ACC AAA AGT TAT     1536
Ser Asp Leu Pro Pro Pro Glu Pro Tyr Val Gln Thr Thr Lys Ser Tyr
495                 500                 505                 510
CCC AGC AAA CTG GCA AGA AAC GAA AGC CGG AGT Gga tcc aac cga aga     1584
Pro Ser Lys Leu Ala Arg Asn Glu Ser Arg Ser Gly Ser Asn Arg Arg
                515                 520                 525
gaa agg ggt ggt cca cca ctc cct ccc atc ccg agg tga tct ttg gct     1632
Glu Arg Gly Gly Pro Pro Leu Pro Pro Ile Pro Arg OPA Ser Leu Ala
                530                 535                 540
gct ctt ctc tac cca agc tca aga gct gct tct gtt ggt atc taa gaa     1680
Ala Leu Leu Tyr Pro Ser Ser Arg Ala Ala Ser Val Gly Ile OCH Glu
                545                 550                 555
ctg gat acc ctc ccc cct                                             1698
Leu Asp Thr Leu Pro Pro
                560
```

FIG. 1B

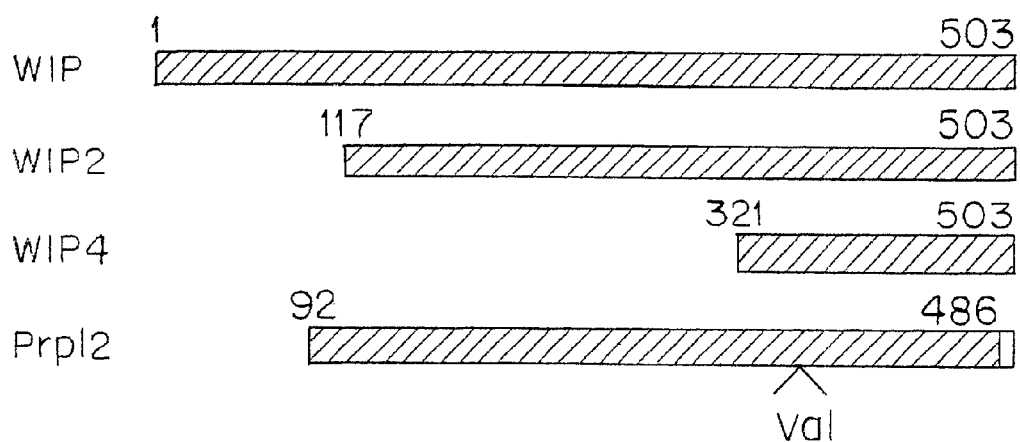
FIG. IC

```
                      ***   ***
     1     MPVPPPPAPP PPPTFALANT EKPTLNKTEQ AGRNALLSDI

SKGKKLKKTV TNDRSAPILD KPKGAGAGGG GGGFGGGGGF

81     GGGGGGGGGG SFGGGGPPGL GGLFQAGMPK LRSTANRDND

SGGSRPPLLP PGGRSTSAKP FSPPSGPGRF PVPSPGHRSG

161     PPEPQRNRMP PPRPDVGSKP DSIPPPVPST PRPIQSSLHN

RGSPPVPGGP RQPSPGPTPP PFPGNRGTAL GGSIRQSPL

241     SSSSPFSNRP PLPPTPSRAL DDKPPPPPPP VGNRPSIHRE

AVPPPPPQNN KPPVPSTPRP SAPHRPHLRP PPPSRPGPPP

321     LPPSSSGNDE TPRLPQRNLS LSSSTPPLPS PGRSGPLPPP

PSERPPPPVR DPPGRSGPLP PPPPVSRNGS TSRALPATPQ

****  **
   401     LPSRSGVDSP RSGPRPPLPP DRPSAGAPPP PPPSTSIRNG

FQDSPCEDEW ESRFYFHPIS DLPPPEPYVQ TTKSYPSKLA

481     RNESRSGSNR RERGGPPLPP IPR
```

FIG. 1D

```
WIP    1   MPVPPPPAPPPPTFALANTEKPTLNKTEQA  GRNALLSDISKGKKLKKTVTNDRSAPILD
           |::|::|||||.  :::::|.|.          |:|:::||||.|||.|||||||||||
Verp   1   MAGAPAPPPPPPPALGGSAPKPA..KSVMQ  GRDALLGDIRKGMKLKKAETNDRSAPIV.

WIP   61   KPKGAGAGGGGGGFGGGGGGGGGGGSFGGG  GPPGLGGLFQAGMPKLR
           |:..:::|::.:::..|                :|.|.|:::|||||
Verp  57   .....GGGVVSSASGSSGTVSSKGPSMSAPPIPGM  GAPQLGDILAGGIPKLK
```

FIG. 1E

| | | | | | | | | | | |
|---|---|---|---|---|---|---|---|---|---|---|
| WIP | 352-361 | G | R | S | G | P | L | P | P | P | P |
| WIP | 374-383 | G | R | S | G | P | L | P | P | P | P |
| WIP | 410-419 | P | R | S | G | P | R | P | P | L | P |
| WASP | 338-347 | G | R | S | G | P | L | P | P | V | P |
| WASP | 376-385 | G | R | S | G | P | L | P | P | P | P |
| Consensus | | G | R | S | G | P | X | P | P | X | P |

FIG. 1F

WIP, A WASP-ASSOCIATED PROTEIN

RELATED APPLICATION(S)

This application is a continuation application of PCT/US98/27501, entitled "WIP, A WASP-ASSOCIATED PROTEIN", filed Dec. 22, 1998, which claims the benefit of U.S. Provisional Application No. 60/101,457 filed Sep. 23, 1998, entitled "WIP, A WASP-ASSOCIATED PROTEIN, INDUCES ACTIN POLYMERIZATION AND REDISTRIBUTION IN LYMPHOID CELLS", and U.S. Provisional Application No. 60/068,533 filed Dec. 23, 1997, entitled "WIP, A WASP-ASSOCIATED PROTEIN, INDUCES ACTIN POLYMERIZATION AND REDISTRIBUTION IN LYMPHOID CELLS". The entire teachings of each application are incorporated herein by reference.

GOVERNMENT SUPPORT

The invention was supported, in whole or in part, by grants AI37130 and AI35714 from National Institutes of Health. The Government has certain rights in the invention.

BACKGROUND OF THE INVENTION

Wiskott-Aldrich Syndrome (WAS) is an X-linked immunodeficiency caused by mutations that affect the WAS protein (WASP). It is characterized by thrombocytopenia, eczema, impaired immunity and a predisposition to develop lymphomas and leukemias (Cooper, M. D., Chase, H. P., Lowman, J. T., Krivit, W. & Good, R. A. (1968) *Am. J. Medicine*, 44: 499–513). The size of platelets and lymphocytes is reduced in WAS and scanning electron microscopy of T lymphocytes shows a relatively smooth surface with decrease in the number and size of microvilli, suggesting a defect in cytoskeletal architecture (Remold-O'Donnell, E. & Rosen, F. S. (1993) in *Sialophorin* (CD43) *and the Wiskott-Aldrich Syndrome*, eds. Rosen, F. S. & Seligmann, M. S. (Harwood Academic Publishers, Chur), pp. 225–241), pp.225–241 (1993)). The WAS gene is located on Xp11.22–Xp11.23 and encodes a 502 amino acid (a.a.) long proline rich protein, WASP (Derry, J. M. J., Ochs, H. D. & Francke, U. (1994) *Cell*, 78. 635–644.). WASP contains an N-terminal pleckstrin homology (PH) domain, which partially overlaps with a WASP homology (WH) domain, WH1, found in several proteins involved in the maintenance of cytoskeletal integrity that include Ena, Mena, Evl and VASP (Gertler, F. B., Niebuhr, K., Reinhard, M., Wehiand, J. & Soriano, P. (1996) *Cell*, 87: 227–239). The WH1 domain in WASP is followed by a GTPase binding domain (GBD/CRIB) (Bunnell, S. C., Henry, P. A., Kolluri, R., Kirchhausen, T., Rickles, R. J. & Berg, L. J. (1996) *J. Biol. Chem.* 271: 25646–25656), a number of proline rich stretches, a second WH domain (WH2), a short verprolin homology sequence, a cofilin homology sequence, and an acidic C-terminal region. Recently, a protein highly homologous to WASP was cloned from bovine brain and was termed N-WASP (Miki, H., Miura, K. & Takenawa, T. (1996) *EMBO J*. 15, 5326–5335). N-WASP has a domain organization similar to that of WASP, and is widely expressed, in contrast to WASP which is expressed only in hematopoietic cells.

WASP binds via its GBD domain to the small molecular weight GTPase Cdc42 and weakly to Rac, but not to Rho (Aspenstrom, P., Lindberg, U. & Hall, A. (1996) *Curr. Biol.* 6: 70–75; Kolluri, R., Tolias, K. F., Carpenter, C. L., Rosen, F. S. & Kirchhausen, T. (1996) *Proc. Natl. Acad. Sci.* (USA) 93: 5615–5618; Symons, M., Derry, J. M. J., Kariak, B., Jiang, S., Lemahieu, V., McCorrnick, F., Francke, U. & Abo, A. (1996) *Cell* 84: 723–734). Cdc42, Rac and Rho regulate cytoskeletal organization (Nobes, C. D. & Hall, A. (1995) *Cell* 81: 53–62). Overexpression of WASP induces the formation of actin-containing clusters (Symons, M., Derry, J. M. J., Kariak, B., Jiang, S., Lemahieu, V., McCormick, F., Francke, U. & Abo, A. (1996) *Cell* 84. 723–734). This is inhibited by dominant negative mutants of Cdc42, but not of Rac or Rho (Symons, M., Derry, J. M. J., Kariak, B., Jiang, S., Lemahieu, V., McCormick, F., Francke, U. & Abo, A. (1996) *Cell* 84: 723–734). These findings suggest that WASP may provide a link between Cdc42, Rac and the cytoskeleton.

WASP interacts with components of signal transduction pathways via their SH3 domains (Src homology 3) which recognize the proline rich domain in WASP (Featherstone, C. (1997) *Science* 275: 27–28). WASP associates with the adaptor protein Nck (Rivero-Lezcano, O. M., Marcilla, A., Sameshima, J. H. & Robbins, K. C. (1995) *Mol. Cell Biol.*, 15: 5725–5731). Nck can be recruited via its SH2 domain to tyrosine phosphorylated receptors (Galisteo, M. L., Chernoff, J., Su, Y.-C., Skolnich, E. Y. & Schlessinger, J. (1996) *J. Biol. Chem.* 271: 20997–21000). WASP also binds in vivo to fyn (Rivero-Lezcano, O. M., Marcilla, A., Sameshima, J. H. & Robbins, K. C. (1995) *Mol. Cell Biol*. 15: 5725–5731; Banin, S., Truong, O., Katz. D. R., Waterfield, M. D., Brickell, P. M. & Gout, I. (1996) *Curr. Biol.*, 6: 981–988) and in vitro to the src kinase fgr, to the tyrosine kinases btk, itk, Abl and to the p85 subunit of PLC-g (Banin, S., Truong, O., Katz. D. R., Waterfield, M. D., Brickell, P. M. & Gout, I. (1996) *Curr. Biol.* 6, 981–988; Molina, I. J., Sancho, J., Terhorst, C., Rosen, F. S. & Remold-O'Donnell, E. (1993) *J. Immunol.*, 151. 4383–4390; Finan, P. M., Soames, C. J., Wilson, L., Nelson, D. L., Stewart, D. M., Truong, O., Hsuan, J. J. & Kellie, S. (1996) *J. Biol. Chem.*, 271: 26291–26295).

It would be helpful to have a better understanding of the function of WASP.

SUMMARY OF THE INVENTION

Described herein is a novel human gene whose 503 amino acid (a.a.) product interacts with WASP. The protein is referred to as WIP, for WASP-interacting protein. The proline-rich WIP, which co-immunoprecipitated with WASP from lymphocytes, has been shown to bind to WASP at a site distinct from the Cdc42 binding site and to have actin, profilin and Nck binding motifs. Expression of WIP in human B cells, but not of a WIP truncation mutant that lacks the actin binding motif, increased polymerized actin content and induced the appearance of actin-containing cerebriform projections on the cell surface. Work described herein supports the role of WIP in cortical actin assembly that may be important for lymphocyte function. Overexpression of WIP increases F-actin content and induces actin containing structures in the human B cell line BJAB, suggesting an important role for WIP in the organization of the actin cytoskeleton.

In particular, the present invention relates to isolated (e.g., purified, essentially pure) nucleic acids (oligonucleotides, polynucleotides, nucleotide sequences) which encode mammalian (e.g., human) WIP, and include for example, nucleic acids (DNA, RNA) which are obtained from natural sources, recombinantly produced or chemically synthesized. The nucleic acids of the present invention include nucleic acids encoding human WIP (SEQ ID NO: 1) and characteristic portions of the nucleic acid sequences (e.g., probes, primers). The invention also includes complementary sequences (i.e., a complement) of SEQ ID NO: 1 and characteristic portions thereof. The nucleic acids of the present invention encompass nucleic acids encoding a human WIP amino acid sequence (SEQ ID NO: 2) and characteristic portions thereof.

The present invention further relates to isolated, recombinantly produced or synthetic nucleic acids which hybridize to the nucleic acids described herein (e.g., the complement of SEQ ID NO: 1 or characteristic portions thereof) and encode WIP (a protein having the same amino acid sequence as the amino acid sequences included herein and/or a protein which exhibits the same characteristics as WIP described herein). In particular, the invention relates to nucleic acids which hybridize, under moderate or high stringency conditions, to SEQ ID NO: 1 characteristic portions thereof or other sequences which encode WIP.

Also encompassed by the present invention is a nucleic acid construct comprising nucleic acid which encodes a WIP (e.g., SEQ ID NO: 1 and characteristic portions thereof), wherein the nucleic acid of the construct is expressed when the construct is present in an appropriate host cell. In one embodiment, the nucleic acid construct of the present invention is operably linked to exogenous regulatory sequence(s) such as a promoter and/or enhancer, whereby mammalian WIP is expressed hen the host cell is maintained under conditions suitable for expression. The present invention also relates to a host cell comprising nucleic acid encoding mammalian WIP.

Also encompassed by the present invention is a method for producing a WIP (mammalian, such as human). In one embodiment, a nucleic acid construct comprising a nucleotide sequence (DNA, RNA) which encodes a WIP is introduced into a host cell, resulting in production of a recombinant host cell which contains a WIP coding sequence operably linked to an (i.e., at least one) expression control sequence. The host cells produced are maintained in a suitable medium under conditions appropriate for the nucleotide sequence to be expressed, whereby the encoded WIP is produced.

The present invention also relates to isolated (e.g., purified, essentially pure) WIP and includes, for example, WIP obtained from natural sources, recombinantly produced or chemically synthesized. For example, the WIP can be human WIP (SEQ ID NO: 2) or functional portions thereof.

Also encompassed by the present invention is an agent which interacts with WIP directly or indirectly, and inhibits or enhances WIP function. In one embodiment, the agent is an inhibitor which interferes with WIP directly (e.g., by binding WIP) or indirectly (e.g., by blocking the ability of WIP to a) bind WASP, profilin and/or Nck; b) increase F-actin content in lymphocytes; c) increase cellular content of polymerized actin; d) increase appearance of cerebriform projections on the cell surface containing F-actin). In a particular embodiment, an inhibitor of the WIP is an antibody specific for WIP protein or a portion of a WIP; that is, the antibody binds the WIP. For example, the antibody can be specific for the human WIP (SEQ ID NO: 2) or functional portions thereof Alternatively, the inhibitor can be an agent other than an antibody (e.g., small organic molecule, protein, peptide) which binds WIP and blocks its activity. Furthermore, the inhibitor can be an agent which mimics WIP structurally but lacks its function. Alternatively, the inhibitor of WIP can be an agent which binds to or interacts with a molecule which WIP normally binds with or interacts with, thus blocking WIP from doing so and preventing it from exerting the effects it would normally exert. In another embodiment, the agent is an enhancer of WIP which increases the activity of WIP (e.g., the ability of WIP to a) bind WASP, profilin and/or Nck; b) increase F-actin content in lymphocytes; c) increase cellular content of polymerized actin; d) increase appearance of cerebriform projections on the cell surface containing F-actin), increases the length of time it is effective (by preventing its degradation or otherwise prolonging the time during which it is active) or both, either directly or indirectly.

The present invention also relates to antibodies (monoclonal or polyclonal) or functional portions thereof (e.g., an antigen binding portion such as an Fv, Fab, Fab', or F(ab')$_2$ fragment) which bind WIP.

WIP DNA fragments can be used as probes (e.g., in hybridization methods) or primers (e.g., in amplification methods). They can be used, for example, to determine whether WIP DNA or RNA is present in cells (e.g., a sample obtained from an individual). For example, WIP DNA can be used as a probe to determine if wild-type (nonmutated) or mutated WIP DNA is present in a sample of cells and also to determine the extent (quantity) to which wild-type and mutated forms occur. Antibodies can also be used as probes to assess cells for the occurrence of WIP.

Isolation of WIP makes it possible to detect WIP in a sample (e.g., test sample). The present invention also relates to a method of detecting WIP in a sample (e.g., blood) obtained from an individual, such as a human. In one embodiment, the sample is treated to render nucleic acids in the sample available for hybridization to a nucleic acid probe (e.g., SEQ ID NO: 1 and/or characteristic portions thereof which bind to characteristic regions of WIP-encoding nucleic acids). The treated sample is combined with a nucleic acid probe (labeled or unlabeled) comprising or complementary to all or a characteristic portion of the nucleotide sequence encoding WIP, under conditions appropriate for hybridization of complementary nucleic acids to occur. Hybridization of nucleic acids in the treated sample with the nucleic acid probe is detected; the occurrence of hybridization indicates the presence of WIP in the sample. In another embodiment, the sample is contacted with an antibody which binds to WIP (e.g., SEQ ID NO: 2 or functional portions thereof) under conditions suitable for binding of the antibody to the mammalian WIP. Binding of the antibody to a component of the sample is detected; binding of the antibody to a component of the sample indicates the presence of WIP protein in the sample.

Isolation of WIP also makes it possible to identify a promoter(s) and/or enhancer(s) of the WIP gene. Identification of promoters and/or enhancers of the WIP gene allow for identification of regulators of WIP transcription.

In addition, the present invention relates to transgenic non-human animals (e.g., mice) which lack the WIP gene or contain a nonfunctional WIP gene such that WIP activity is lacking (e.g., WIP knockout mouse). The invention also relates to methods of producing WIP gene knockout animals, such as mice. WIP knockout mice can be used to further study the WIP gene and to assay for inhibitors and enhancers of WIP.

Methods of altering actin content, actin polymerization or both, methods of altering or regulating WASP function and methods of treating conditions in which WIP and/or WASP and/or their respective DNAs are deficient and/or defective are also the subject of this invention. In the methods, WIP or DNA encoding WIP can be administered to an individual, by known methods, in sufficient quantity to alter actin content and/or the extent to which polymerization occurs and, thus,

BRIEF DESCRIPTION OF THE DRAWINGS

FIGS. 1A–1B are the nucleotide sequence of WIP cDNA (SEQ ID NO: 1).

FIG. 1C is a schematic representation of full length WIP, WIP2, WIP4 and Prp12 cDNAs. The open box in Prp12 represents the 7 a.a. that replace the C-terminal 17 a.a. in WIP.

FIG. 1D is the deduced amino acid (a.a.) sequence of WIP (SEQ ID NO.: 2). The two APPPPP (SEQ ID NO: 3) motifs implicated in profilin binding are denoted by asterisks. A line is drawn over the KLKK (SEQ ID NO: 4) motif implicated in actin binding.

FIG. 1E is the sequence alignment of the N terminal regions of WIP (SEQ ID NO.: 5) and verprolin (SEQ ID NO.: 6). The two verprolin homology regions are boxed.

FIG. 1F is the sequence alignment of GRSGPXPPXP (SEQ ID NO: 7) motifs in WIP 352–361 (SEQ ID NO: 8), WIP 374–383 (SEQ ID NO: 9), WIP 410–419 (SEQ ID NO: 10), WASP 338–347 (SEQ ID NO: 11) and WASP 376–385 (SEQ ID NO: 12). Numbers refer to a.a. positions.

DETAILED DESCRIPTION OF THE INVENTION

Figure 2A:
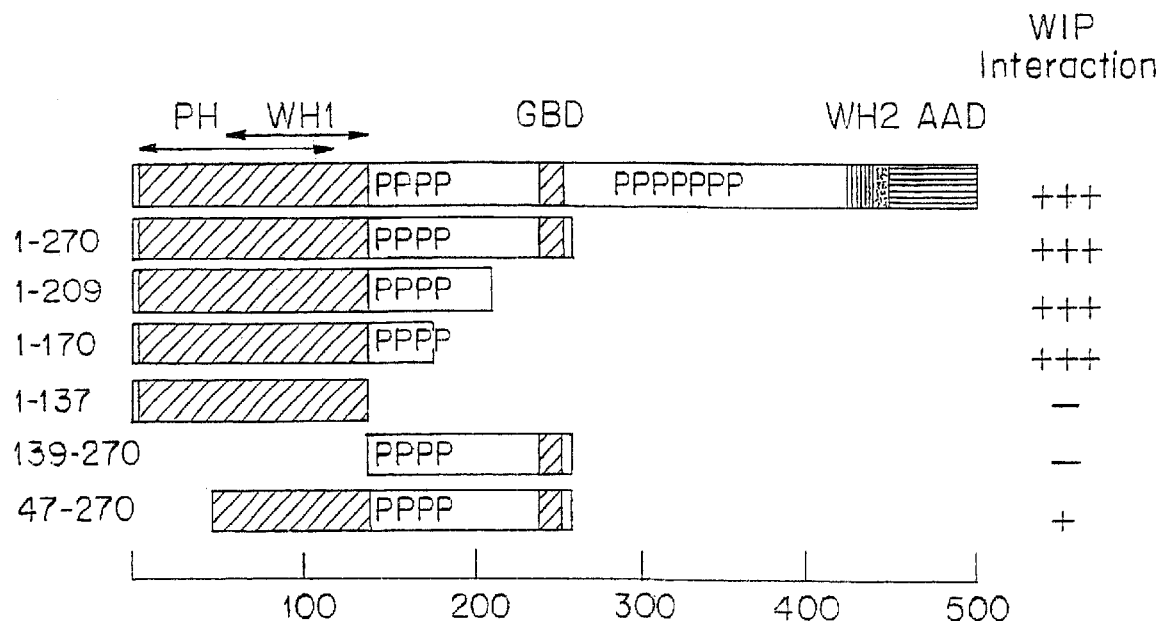
FIG. 2A is a mapping of the WIP binding site of WASP. The domains of WASP are indicated. PH: Pleckstrin homology domain (a.a. 6–105); WH1: WH1 domain (a.a. 47–137); pppppp (SEQ ID NO: 13) :proline rich region; GBD: GTPase binding domain (a.a. 238–257); WH2: WH2 domain (a.a. 423–449); AAD: actin association domain (a.a. 443–502). The numbers under the bar at the bottom of the diagram represent the a.a of WASP. Truncation mutants of WASP, generated either by PCR or by cleavage with appropriate restriction enzymes, were cloned into the pGBT9 vector and examined for WIP binding in the yeast two hybrid system. Blue color development by β-galactosidase activity was used to score the interaction of WIP with WASP truncations. +++ represents color change in 30 min. or less, + represents color change in 3 h and—indicates no color change and lack of growth in His⁻ medium. For each mutant at least three independent colonies were tested in the β-galactosidase assay.

Described herein is a novel gene and its product, WIP, which associates with WASP. The subject invention relates to the isolated WIP gene or cDNA (see FIGS. 1A–1B); nucleic acid probes, which can be fragments of the WIP gene or WIP cDNA or full-length; nucleic acid primers, which are fragments of WIP cDNA or the WIP gene; methods of assessing cells (e.g., for diagnostic purposes) for the presence of WIP DNA, (e.g., wildtype or mutated) or for the absence or occurrence of a reduced level of WIP DNA; WIP mRNA; WIP or WIP fragments, such as those which are useful to generate antibodies which bind WIP; and antibodies which bind WIP. Also the subject of this invention are methods of treating conditions in which WIP and/or WASP DNA or protein is deficient (in quantity) and/or defective (e.g., mutated/altered) such that an individual is adversely affected (e.g., has Wiskott-Aldrich Syndrome); methods of altering or regulating WASP and its functions; and methods of altering actin content, actin polymerization or both in cells, such as human lymphoid cells (e.g., β lymphocytes). A further subject of this invention is an assay to identify drugs which alter (e.g., enhance) the activity of WIP or expression of WIP DNA.

Isolated WIP DNA comprises DNA whose sequence is represented herein (e.g., SEQ ID NO.: 1), DNA which is the complement of WIP DNA of SEQ ID NO.: 1; DNA which encodes a WIP (e.g., DNA which encodes WIP as represented in SEQ ID NO.: 2) and DNA which hybridizes to WIP DNA or to a WIP DNA complement. WIP RNA is also the subject of this invention. Isolated WIP is another subject of this invention and includes the amino acid sequence SEQ ID NO.: 2, shown in FIG. 1D, and other amino acid sequences which are sufficiently similar to that of SEQ ID NO.: 2 that they have substantially the same characteristics and functions as described herein for WIP. DNA, RNA and protein are referred to herein as "isolated", which is intended to include DNA, RNA and protein obtained from (isolated from) sources in which they occur in nature, as well as DNA, RNA and protein produced by recombinant or chemical synthetic methods. The WIP DNA, RNA and protein can be of vertebrate, including mammalian, such as human, origin.

The present invention relates to isolated (e.g., purified, essentially pure) WIP gene which is involved in actin polymerization and redistribution in mammals. In particular, the present invention relates to nucleic acids (e.g., DNA, RNA, oligonucleotides, polynucleotides) or characteristic portions thereof as described herein, obtained from natural sources, recombinantly produced or chemically synthesized which encode a WIP or functional portion thereof.

Nucleic acids referred to herein as "isolated" are nucleic acids substantially free of (separated away from) the nucleic acids of the genomic DNA or cellular RNA of their biological source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis or by combinations of biological and chemical methods, and recombinantly produced nucleic acids which are isolated (see e.g., Daugherty, B. L. et al., *Nucleic Acids Res.*, 19(9):2471–2476 (1991); Lewis, A. P. and J. S. Crowe, *Gene*, 101: 297–302 (1991)). Nucleic acids referred to herein as "recombinant" are nucleic acids which have been produced by recombinant DNA methodologies (recombinantly produced). Recombinant DNA methodologies include, for example, expression of WIP in a host cell containing or modified to contain DNA or RNA encoding WIP or expression of WIP using polymerase chain reaction (PCR) techniques.

This invention includes characteristic portions of the nucleic acids described herein. As used herein, a "characteristic portion" of nucleic acids described herein refers to portions of a nucleotide sequence which encode a protein or polypeptide having at least one property, function or activity characteristic of WIP (e.g., the ability of WIP a) to bind WASP, profilin and/or Nck; b) increase F-actin content in lymphocytes; c) increase cellular content of polymerized actin; d) increase appearance of cerebriform projections the on cell surface containing F-actin). In addition, the term includes a nucleotide sequence which, through the degeneracy of the genetic code, encodes the same peptide as a peptide whose sequence is presented herein (e.g., SEQ ID NO: 1). The nucleic acids described herein may also contain a modification of the molecule such that the resulting gene product is sufficiently similar to that encoded by the unmodified sequence that it has essentially the same activity as the unmodified sequence. An example of such a modification would be a "silent" codon substitution or an amino acid substitution, for instance, substitution of one codon encoding a hydrophobic amino acid to another codon encoding the same hydrophobic amino acid or substitution of one acidic amino acid for another acidic amino acid. See Ausubel, F. M., et al., *Current Protocols in Molecular Biology*, Greene Publ. Assoc. and Wiley-Interscience 1989.

In one embodiment, the nucleic acid or characteristic portion thereof encodes a protein or polypeptide having at least one property, activity or function characteristic of a WIP (as defined herein), such as activity or function characteristic of a WIP (as defined herein), such as the ability of WIP to a) bind WASP, profilin and/or Nck; b) increase F-actin content in lymphocytes; c) increase cellular content of polymerized actin; d) increase appearance of cerebriform projections on the cell surface containing F-actin. In a particular embodiment the characteristic portion which encodes a protein or polypeptide having at least one property, activity or function characteristic of WIP comprises at least 10 consecutive nucleotides in the coding region of SEQ ID NO: 1 which are 5' of nucleotide 380 of SEQ ID NO: 1.

The present invention also relates more specifically to isolated nucleic acids or a characteristic portion thereof, which encode mammalian WIP or variants thereof.

The invention relates to isolated nucleic acids that:
(1) hybridize to (a) a nucleic acid encoding a WIP (e.g., human), such as a nucleic acid having a nucleotide sequence as set forth or substantially as set forth in FIGS. 1A–1B (SEQ ID NO:1); (b) the complement of the sequence of (a); or (c) characteristic portions of either of the foregoing (e.g., a portion comprising the open reading frame);
(2) encode a protein or polypeptide having at least one property, activity of function characteristic of a WIP protein (e.g., the ability of WIP to a) bind WASP, profilin and/or Nck; b) increase F-actin content in lymphocytes; c) increase cellular content of polymerized actin; d) increase appearance of cerebriform projections on the cell surface containing F-actin)
(3) encode a polypeptide having the amino acid sequence of a mammalian WIP (e.g., SEQ ID NO: 2); or
(4) have a combination of these characteristics.

In one embodiment, the nucleic acid shares at least about 75% nucleotide sequence similarity, preferably 80%–85% nucleotide sequence similarity and more preferably, at least about 90% nucleotide sequence similarity, to the sequence shown in FIGS. 1A–1B (SEQ ID NO:1). Isolated nucleic acids meeting these criteria include nucleic acids having sequences identical to sequences of naturally occurring mammalian WIP.

The present invention also relates to variants of the naturally occurring sequences which encode WIP (e.g., mammalian, such as human). Such variants include mutants differing by the addition, deletion or substitution of one or more residues, modified nucleic acids in which one or more residues are modified (e.g., DNA or RNA analogs), and mutants comprising one or more modified residues.

Nucleic acids of the present invention may be RNA or DNA (e.g., cDNA, genomic DNA, and synthetic DNA). The DNA may be double-stranded or single-stranded and, if single stranded, may be the coding strand or non-coding (anti-sense) strand. The coding sequence which encodes the polypeptide may be identical to the coding sequence shown in FIGS. 1A–1B (SEQ ID NO:1) or may be a different coding sequence which, as a result of the redundancy or degeneracy of the genetic code, encodes the same polypeptide as the polypeptide encoded by the DNA of FIGS. 1A–1B.

The nucleic acid (polynucleotide) which encodes a WIP polypeptide encoded by the WIP cDNA may include: only the coding sequence of a polypeptide; the coding sequence for a polypeptide and additional coding sequence such as a leader or secretory sequence; the coding sequence for a polypeptide (and optionally additional coding sequence) and non-coding sequence, such as introns or non-coding sequence 5' and/or 3' of the coding sequence.

Nucleic acids of the present invention, including those which hybridize to a selected nucleic acid as described above, can be detected or isolated under high stringency conditions or moderate stringency conditions, for example. "High stringency conditions" and "moderate stringency conditions" for nucleic acid hybridizations are explained at pages 2.10.1–2.10.16 (see particularly 2.10.8–11) and pages 6.3.1–6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, and depend in part upon the characteristics of the known nucleic acid (e.g., DNA) and the other nucleic acids to be assessed for hybridization thereto.

Nucleic acids of the present invention that are characterized by their ability to hybridize (e.g., under high or moderate stringency conditions) to (a) a nucleic acid encoding a WIP (for example, the nucleic acid depicted in FIGS. 1A–1B (SEQ ID NO:1) or characteristic portions thereof); (b) the complement of the nucleic acids of (a); or (c) a portion thereof, can also encode a protein or polypeptide having at least one property, activity or function characteristic of a mammalian WIP as defined herein, such as the ability of WIP to a) bind WASP, profilin and/or Nck; b) increase F-actin content in lymphocytes; c) increase cellular content of polymerized actin; c) increase appearance of cerebriform projections on the cell surface containing F-actin. In one embodiment the nucleic acid encodes a polypeptide which retains substantially the same biological function or activity as the polypeptide encoded by the DNA of FIGS. 1A–1B (SEQ ID NO:1). In another embodiment, the nucleic acid encodes a WIP and hybridizes under stringent conditions with at least 10 consecutive nucleotides in the coding region of the complement strand of SEQ ID NO: 1 which are 5' of nucleotide 380 of the complement of SEQ ID NO: 1.

Nucleic acids of the present invention can be used in the production of proteins or polypeptides. For example, a nucleic acid (e.g., DNA) encoding a mammalian WIP can be incorporated into various constructs and vectors created for further manipulation of sequences or for production of the encoded polypeptide in suitable host cells as described above.

A further embodiment of the invention is antisense nucleic acid, which is complementary, in whole or in part, to a WIP sense strand, and can hybridize with it. The antisense strand hybridizes to DNA, or its RNA counterpart (i.e., wherein T residues of the DNA are U residues in the RNA counterpart). When introduced into a cell, antisense nucleic acid hybridizes to and inhibits the expression of the sense strand. Antisense nucleic acids can be produced by standard techniques.

In another embodiment, the antisense nucleic acid is wholly or partially complementary to and can hybridize with a target nucleic acid which encodes a mammalian WIP. For example, antisense nucleic acid can be complementary to a target nucleic acid having the sequence shown as the open reading frame in FIGS. 1A–1B (SEQ ID NO:1) or to a portion thereof sufficient to allow hybridization.

The nucleic acids can also be used as probes (e.g., for in situ hybridization) to assess the presence of levels of WIP in a host. The nucleic acids can also be used as probes to detect and/or isolate (e.g., by hybridization with RNA or DNA) polymorphic or allelic variants, for example, in a sample (e.g., blood, such as peripheral blood mononuclear cells (PMBC)) obtained from a host (e.g., a human). Moreover, the presence or level of a particular variant in a sample(s) obtained from an individual, as compared with the presence or level in a sample(s) from normal individuals, can be indicative of an association between a disease or condition and a particular variant, which in turn can be used in the diagnosis of the disease or condition.

The present invention also relates to isolated (e.g., pure, essentially pure) proteins or polypeptides designated WIP and variants of WIP. In a preferred embodiment, the isolated proteins of the present invention have at least one property, activity or function characteristic of a WIP (as defined herein), such as the ability of WIP to a) bind WASP, profilin and/or Nck; b) increase F-actin content in lymphocytes; c) increase cellular content of polymerized actin; d) increase appearance of cerebriform projections on the cell surface containing F-actin.

Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods. They include essentially pure proteins or polypeptides, proteins or polypeptides produced by chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein, "WIP" protein refers to naturally occurring or endogenous WIPs, proteins having an amino acid sequence which is the same as that of a naturally occurring or endogenous corresponding WIP (e.g., recombinant proteins).

In addition, the present invention relates to functional variants of each of the foregoing (e.g., functional fragments and/or mutants produced via mutagenesis and/or recombinant techniques). Accordingly, the present invention relates to WIP, glycosylated or unglycosylated WIP, polymorphic or allelic variants, and other isoforms of WIP (e.g., produced by alternative splicing or other cellular processes), and functional fragments.

Naturally occurring or endogenous WIPs include wild type proteins such as WIP, polymorphic or allelic variants and other isoforms which occur naturally in mammals (e.g., primate, preferably human, murine, bovine). Such proteins can be recovered from a source in which WIP is naturally produced, for example. These mammalian proteins have the same amino acid sequence as naturally occurring or endogenous corresponding mammalian WIP.

"Functional variants" of WIP include functional fragments, functional mutant proteins, and/or functional fusion proteins. Generally, fragments or portions of WIP encompassed by the present invention include those having one or more amino acid deletions relative to the naturally occurring WIP (such as N-terminal, C-terminal or internal deletions). Fragments or portions in which only contiguous amino acids have been deleted or in which non-contiguous amino acids have been deleted relative to naturally occurring WIP are also encompassed by the invention.

Generally, mutants or derivatives of WIP, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. For example, mutants can be natural or artificial variants of WIP which differ from naturally occurring WIP by the addition, deletion and/or substitution of one or more contiguous or non-contiguous amino acid residues.

A "functional fragment or portion", "functional mutant" and/or "functional fusion protein" of a WIP refers to an isolated protein or oligopeptide which has at least one property, activity or function characteristic of a mammalian WIP, such as the ability of WIP to a) bind WASP, profilin and/or Nck; b) increase F-actin content in lymphocytes; c) increase cellular content of polymerized actin; d) increase appearance of cerebriform projections on the cell surface containing F-actin.

Suitable fragments or mutants can be identified by screening. For example, the N-terminal, C-terminal, or internal regions of the protein can be deleted in a step-wise fashion and the resulting protein or polypeptide can be screened using a suitable assay, for example, by measuring the ability of the fragment or mutant to bind WASP, profilin and/or Nck; increase F-actin content in lymphocytes; increase cellular content of polymerized actin; increase appearance of cerebriform projections on cell surface containing F-actin. Where the resulting protein displays activity in the assay, the resulting protein ("fragment") is functional.

The invention also encompasses fusion proteins, comprising a WIP as a first moiety, linked to a second moiety not occurring in the WIP found in nature. Thus, the second moiety can be, for example, an amino acid, oligopeptide or polypeptide. The first moiety can be in an N-terminal location, C-terminal location or internal location of the fusion protein. In one embodiment, the fusion protein comprises a WIP or portion thereof as the first moiety, and a second moiety comprising an affinity ligand (e.g., an enzyme, an antigen, epitope tag) joined to the first moiety. Optionally, the two components can be joined by a linker.

Examples of "human WIP" include proteins having an amino acid sequence as set forth or substantially as set forth in FIG. 1D (SEQ ID NO: 2) and functional portions thereof. In preferred embodiments, a human WIP or a variant thereof has an amino acid sequence which has at least about 75% identity, preferably at least about 85% identity and more preferably at least about 90% identity, to the protein shown in FIG. 1D (SEQ ID NO: 2).

Another aspect of the invention relates to a method of producing a WIP or variant (e.g., portion) thereof. Recombinant protein can be obtained, for example, by the expression of a recombinant DNA molecule encoding a WIP or variant thereof in a suitable host cell.

Constructs suitable for the expression of a WIP or variant thereof are also provided. The constructs can be introduced into a suitable host cell, and cells which express a recombinant WIP or variant thereof, can be produced and maintained in culture. Such cells are useful for a variety of purposes, and can be used in the production of protein for characterization, isolation and/or purification, (e.g., affinity purification), and as immunogens, for instance. Suitable host cells can be procaryotic, including bacterial cells such as *E. coli, B. subtilis* and or other suitable bacteria (e.g., Streptococci) or eucaryotic, such as fungal or yeast cells (e.g., *Pichia pastoris, Aspergillus species, Saccharomyces cerevisiae, Schizosaccharomyces pombe, Neurospora crassa*), or other lower eucaryotic cells, and cells of higher eucaryotes such as those from insects (e.g., Sf9 insect cells) or mammals (e.g., Chinese hamster ovary cells (CHO), COS cells, HuT 78 cells, 293 cells). (See, e.g., Ausubel, F. M. et al., eds. *Current Protocols in Molecular Biology*, Greene Publishing Associates and John Wiley & Sons Inc., (1993)).

Host cells which produce a recombinant WIP or variants thereof can be produced as follows. For example, nucleic acid encoding all or part of the WIP or a functional portion thereof can be inserted into a nucleic acid vector, e.g., a DNA vector, such as a plasmid, virus or other suitable replicon for expression. A variety of vectors is available, including vectors which are maintained in single copy or multiple copy, or which become integrated into the host cell chromosome.

The transcriptional and/or translational signals of a mammalian WIP gene can be used to direct expression. Alternatively, suitable expression vectors for the expression of a nucleic acid encoding all or part of the desired protein are available. Suitable expression vectors can contain a number of components, including, but not limited to, one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion (of mammalian origin or from a heterologous mammal or non-mammalian species). In a construct, a signal sequence can be provided by the vector, the WIP coding sequence, or other source.

A promoter can be provided for expression in a suitable host cell. Promoters can be constitutive or inducible. The promoter is operably linked to nucleic acid encoding the WIP or variant thereof, and is capable of directing expression of the encoded polypeptide in the host cell. A variety of suitable promoters for procaryotic (e.g., lac, tac, T3, T7 promoters for *E. coli*) and eucaryotic (e.g., yeast alcohol dehydrogenase (ADH1), SV40, CMV) hosts is available.

In addition, the expression vectors typically comprise a selectable marker for selection of host cells carrying the vector, and in the case of a replicable expression vector, also comprise an origin of replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid encoding a mammalian WIP or variant thereof is incorporated into a vector, operably linked to one or more expression control elements, and the construct is introduced into host cells which are maintained under conditions suitable for expression, whereby the encoded polypeptide is produced. The construct can be introduced into cells by a method appropriate to the host cell selected (e.g., transformation, transfection, electroporation, infection). For production of a protein, host cells comprising the construct are maintained under conditions appropriate for expression, (e.g., in the presence of inducer, suitable media supplemented with appropriate salts, growth factors, antibiotic, nutritional supplements, etc.). The encoded protein (e.g., human WIP) can be isolated from the host cells or medium.

Fusion proteins can also be produced in this manner. For example, some embodiments can be produced by the insertion of a WIP cDNA or portion thereof into a suitable expression vector, such as Bluescript® II SK +/− (Stratagene), pGEX-4T-2 (Pharmacia), pcDNA-3 (Invitrogen) and pET-15b (Novagen). The resulting construct can then be introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1–16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

As described in the Examples, a cDNA library constructed from a human lymphoma T cell line was screened using full-length WASP cDNA obtained from peripheral blood T cells to identify novel WASP interacting protein(s). This resulted in identification of six clones. The two largest cDNAs, designated WIP2 (1.7 kb) and WIP4 (1.6 kb), were further characterized. See Example 1. WIP2 and WIP4 cDNAs were shown to be the products of the same gene; the WIP4 protein coding sequence was completely contained within WIP2. FIG. 1C is a schematic representation of full-length WIP, WIP2, WIP4 cDNAs, as well as Prp12 cDNA, which is a partial human cDNA isolated from tonsillar B cells whose function is unknown.

The amino acid sequence of WIP is represented in FIG. 1D. The predicted WIP protein product is a 503 a.a. long proline-rich protein with a calculated molecular weight of approximately 52 kd. Analysis of the WIP protein product showed that the N-terminal region contains two stretches (28 and 17 amino acid residues in length) that are highly homologous to corresponding stretches in the N-terminal region of the yeast protein verprolin, which is involved in cytoskeletal organization. The first WIP verprolin homology domain includes the motif KLKK (SEQ ID NO: 4), which was originally identified in thymosin-β4 as a motif critical for actin binding. This further supports direct interaction of WIP with actin. WIP also contains two APPPPP (SEQ ID NO: 3) sequences (denoted by asterisk in FIG. 1D) which have been shown to bind profilin, a protein that regulates actin polymerization.

Further analysis showed that WIP contains putative SH3 binding motifs with the sequence PPPYXP and a unique proline-rich motif, GRSGPXPPXP (SEQ ID NO: 7), which is repeated three times in WIP. (See FIG. 1F) The latter motif occurs twice in WASP and has been implicated in binding of WASP to the SH3 domain-containing proteins fyn, fgr and phospholipase. The presence of conserved SH3 binding domains in WIP suggests WIP may link the signal transduction machinery to the cytoskeleton.

Work also described herein showed that WIP associates with WASP in vitro and in vivo. (See Example 2) The WIP binding site was identified by examining truncations of WASP, as also described in Example 2. Results show that the WIP binding region lies within the N-terminal 170 amino acid residues of WASP (FIG. 2A). This region lacks the GBD domain (amino acids 238–257) and, thus, the WIP binding site on WASP is distinct from the Cdc42 binding site. Both the WH1 domain and the proline-rich amino acid 139–270 region were shown to be necessary, but not sufficient, for WIP binding. The affinity of WASP for WIP was sharply reduced when the N terminal 46 amino acids were deleted (resulting in disruption of the PH domain but not the WH1 domain). This suggests that amino acid residues 1–46 are required for optimal binding of WASP to WIP.

Also described in Example 2 is identification of the WASP binding region of WIP. The carboxy terminal amino acid residue of WIP (in WIP4, amino acid residues 321–503) are sufficient for WASP binding. Initial analysis showed that WASP binding region lies within amino acid residues 377–503 of WIP. Further analysis showed that the WASP binding region lies within amino acid residues 415 to 488.

As described in Example 3, expression of WIP transcripts in human tissues was assessed, using full-length WIP cDNA as probe. Results show that three species of mRNA (estimates sizes 2.4 kb, 3.5 kb, 5 kb) are present in all tissues tested. The different mRNA species appear to be splice variants. WASP is not expressed in non-hematopoietic tissues, suggesting WIP has interactions with partners other than WASP.

Expression of WIP has been shown to cause actin polymerization, as described in Example 4. There was an increase in baseline F-actin content in β lymphocytes that overexpressed full length WIP, but not in control transfected cells. The N-terminal region of WIP was required for the effect of WIP overexpression on F-actin content. Overexpression of WIP4 which lacks the first 320 amino acid residues and, therefore, lacks the actin binding KLKK (SEQ ID NO: 4) motif and one of two profilin binding ABM-2 sequences, did not cause an increase in F-actin content. WIP has also been shown to bind profilin, which has a critical role in actin polymerization. (See Example 5).

WIP mRNA is expressed in many tissues, although its level of expression varies between tissues. The finding that WASP is expressed only in hematopoietic cells suggests that WIP may interact with partners other than WASP, e.g. N-WASP, which we recently showed to interact with WIP. Overexpression of WIP exerts powerful effects on the actin cytoskeleton. These include increase in the cellular content of polymerized actin and appearance of cerebriform projections on the cell surface containing F-actin. The effects of WIP overexpression on the actin cytoskeleton required the N-terminal end of the molecule (a.a. 320), which contains the actin binding KLKK (SEQ ID NO: 4) motif. A number of proteins have been shown to assemble into a spatial actin monomer delivery system. These proteins, which include Mena and VASP, bind profilin via a proline rich ABM-2 motif, XPPPPP (SEQ ID NO: 14), where X denotes G, A, L or S (Gertler, F. B., Niebuhr, K., Reinhard, M., Wehland, J. & Soriano, P. (1996) *Cell*, 87: 227–239; Purich, D. L. and Southwick, F. S. (1997) *Biochem. Biophys. Res. Comm.*, 231:686–691; Reinhard, M., Giehl, K., Abel, K., Haffner, C., Jarchau, T., Hoppe, V., Jockusch, B. M. & Walter, U. (1995) *EMBO J.*, 14 1583–1589). The sequence APPPPP (SEQ ID NO: 3) is represented twice in WIP, once at the N-terminal end and once in the C-terminal region (FIG. 1D). Immobilized WIP bound profilin from cell lysates, suggesting a direct interaction of WIP with profilin. Recombinant profilin was affinity precipitated from bacterial cell lysates by MBP-WIP, further indicating that WIP interacts directly with profilin. Thus, WIP may modulate actin dynamics by direct interaction with actin, via the KLKK (SEQ ID NO: 4) motif, as well as with profilin, and possibly with other proteins that regulate actin polymerization, such as WASP.

The platelet and lymphocyte structural abnormalities in WAS support a functional link between WASP and the actin cytoskeleton. In addition, T lymphocytes from WAS patients fail to proliferate to immobilized anti-CD3 (Molina, I. J., Sancho, J., Terhorst, C., Rosen, F. S. & Remold-O'Donnell, E. (1993) *J. Immunol.*, 151: 4383–4390), a response which depends on actin cytoskeleton rearrangement (Parsey, M. V. & Lewis, G. K. (1993) *J. Immunol.*, 151: 1881–1893; Phatak, P. D. & Packman, C. H. (1 994) *J. Cell. Physiol.*, 159: 365–370). The mechanism by which WASP modulates the actin cytoskeleton is unclear. Although WASP overexpression induces the actin clusters that contain WASP (Symons, M., Derry, J. M. J., Kariak, B., Jiang, S., Lemahieu, V., McCormick, F., Francke, U. & Abo, A. (1996) *Cell*, 84: 723–734), no evidence exists for direct interaction between WASP and actin; however, N-WASP has been shown to interact with actin in vitro (Symons, M., Derry, J. M. J., Kariak, B., Jiang, S., Lemahieu, V., McCormick, F., Francke, U. & Abo, A. (1996) *Cell*, 84: 723–734). WIP binds WASP and overexpression of WIP induces actin cytoskeletal changes. Therefore, WIP may play an important role in linking WASP to the actin cytoskeleton. The actin binding KLKK (SEQ ID NO: 4) motif and one of the two profilin binding ABM-2 motifs in WIP are located in proximity to each other, just as they are in members of the Ena/VASP family. Simultaneous binding of profilactin by WIP may promote actin polymerization by increasing the local concentration of actin monomers. Actin polymerization by a WASP-WIP complex may further be enhanced by the recruitment of profilin to the ABM-2 motifs in WASP.

Cytoskeletal rearrangement is triggered by a variety of signaling pathways induced by external stimuli, such as growth factors, stress and adhesion through integrins (Zigmond, S. H. (1996) *Curr. Opin. Cell. Biol.*, 8: 66–73), and is mediated by small GTPases. WIP does not contain any discernable GBD domain; thus direct interaction of WIP with GTPases is unlikely. However, WASP may bridge Cdc42 to WIP, allowing Cdc42 to regulate WIP function. The WASP-WIP complex may be targeted by stimuli that activate Cdc42 to locate to the actin cytoskeleton via interactions between the WH1 domain of WASP and the proline rich ABM-1 motifs of structural proteins such as zyxin and vinculin (Purich, D. L. and Southwick, F. S. (1997) *Biochem. Biophys. Res. Comm.*, 231:686–691). The presence of SH3 binding motifs in both WIP and WASP suggests that the WASP-WIP complex couples additional signaling pathways to the actin cytoskeleton.

WIP also binds to Nck, an adaptor protein, and induces actin clusters after PDGF stimulation (see Example 6). Nck is a ubiquitous adaptor molecule composed of three Src homology 3 (SH3) domains followed by a single SH2 domain. Via its SH2 domain, Nck links tyrosine phosphorylated receptors to effector proteins that contain SH3 domain binding proline-rich sequences. Recombinant Nck has been demonstrated to have precipitated endogenous WIP, which is a proline-rich protein, from BJAB cell lysates. Nck binds to WIP, through its second SH3 domain, at a site (a.a. 321 to 415) different from the WASP binding site (a.a. 416 to 488). As discussed herein, WIP has been shown to associate with the actin polymerization regulatory protein, profilin, and to induce actin polymerization and cytoskeletal reorganization in lymphoid cells. PDGF stimulation induces ruffles formation mediated by activation of the small GTPase Rac. The over-expression of WIP in 3T3 fibroblasts has been demonstrated to induce actin clustering after PDGF stimulation. The presence of profilin in Nck precipitates indicates that Nck couples extracellular signals to the cytoskeleton via its interaction with WIP and profilin.

WIP has also been demonstrated to complement verprolin function in yeast cells. The ability of WIP to complement verprolin is dependent on the actin-binding amino terminal region of the molecule. WIP shows moderate homology to the yeast protein verprolin. However, the N-terminal region of WIP and verprolin are highly conserved. Verprolin is involved in cytoskeletal organization because vrp1 conditional mutants fail to grow at the restrictive temperature of 37° C., have abnormal actin cytoskeletal organization, show defective bud formation, and have defects in endocytosis. Both WIP and verprolin affect the actin based cytoskeleton. It is likely that WIP is the functional equivalent of verprolin as WIP has been shown to complement the growth, the endocytotic function, and the induction of bipolar budding in vrp1 mutant yeast cells.

The WIP nucleic acids (DNA, RNA) and protein can be used in a variety of ways. It is known that 13% of WAS patients who survive beyond infancy are susceptible to lymphoreticular malignancies (Ochs, H. D., 1998. The Wiskott-Aldrich Syndrome. *SpringerSemin. Immunopathol.*, 19:435–458) suggesting that WASP and by extension WIP has a role in the etiology of some cancers. Since WIP has the potential to bind many cellular signaling molecules (e.g., SH3 containing proteins as exemplified by Nck binding), it is likely that WIP participates in the coordination of processes such as gene transcription adhesion motility, etc. Many of these essential processes display impaired regulation in cancer. Therefore, it is likely that WIP plays a role in cancer and therefore, agents which alter the effect of WIP can be used in the treatment of cancer.

Furthermore, WIP nucleic acids and proteins can be used to identify agents (e.g., molecules) that alter or modulate (enhance, inhibit) WIP expression and/or function. For example, WIP can be expressed in a host cell and effects of test compounds on the ability of WIP to bind WASP, profilin and/or Nck; increase F-actin content in lymphocytes; increase cellular content of polymerized actin; and/or increase appearance of cerebriform projections on cell surface containing F-actin in the host cell could be assessed using the methods described herein.

In one embodiment, the present invention relates to a method of identifying an agent which alters WIP activity, wherein a nucleic acid construct comprising nucleic acid which encodes a WIP is introduced into a host cell(s). The host cells produced are maintained under conditions appropriate for expression of the encoded WIP, whereby the nucleic acid is expressed. The host cells are then contacted with a compound to be assessed (an agent) and the ability of WIP to bind WASP, profilin and/or Nck; increase F-actin content in lymphocytes; increase cellular content of polymerized actin; increase appearance of cerebriform projections on cell surface containing F-actin in the cells is detected in the presence of the compound to be assessed.

A control can be used in the methods of detecting agents which alter WIP activity. For example, the control sample includes the same reagents but lacks the compound or agent being assessed; it is treated in the same manner as the test sample.

Also encompassed by the present invention is an agent which interacts with WIP directly or indirectly, and inhibits or enhances WIP expression and/or function. In one embodiment, the agent is an inhibitor which interferes with WIP directly (e.g., by binding WIP) or indirectly (e.g., by blocking the ability of WIP to function). In a particular embodiment, an inhibitor of WIP is an antibody specific for WIP or a functional portion of WIP; that is, the antibody binds the WIP protein. For example, the antibody can be specific for the protein encoded by the amino acid sequence of human WIP (SEQ ID NO: 2) or portions thereof. Alternatively, the inhibitor can be an agent other than an antibody (e.g., small organic molecule, protein or peptide) which binds WIP and blocks its activity. For example, the inhibitor can be an agent which mimics WIP structurally, but lacks its function. Alternatively, it can be an agent which binds to or interacts with a molecule which WIP normally binds with or interacts with, thus blocking WIP from doing so and preventing it from exerting the effects it would normally exert.

In another embodiment, the agent is an enhancer of WIP which increases the activity of WIP (increases the effect of a given amount or level of WIP), increases the length of time it is effective (by preventing its degradation or otherwise prolonging the time during which it is active) or both either directly or indirectly. For example, WIP nucleic acids and proteins can be used to identify agents which enhance the ability of WIP to bind WASP, profilin and/or Nck; increase F-actin content in lymphocytes; increase cellular content of polymerized actin; increase appearance of cerebriform projections on the cell surface containing F-actin.

In another embodiment, the sequences described herein can be used to detect WIP or DNA encoding WIP in a sample. For example, a labeled nucleic acid probe having all or a functional portion of the nucleotide sequence of WIP can be used in a method to detect WIP in a sample. In one embodiment, the sample is treated to render the nucleic acids in the sample available for hybridization to a nucleic acid probe, which can be DNA or RNA. The resulting treated sample is combined with a labeled nucleic acid probe having all or a portion of the nucleotide sequence of WIP, under conditions appropriate for hybridization of complementary sequences to occur. Detection of hybridization of nucleic acids from the sample with the labeled nucleic probe indicates the presence of WIP in a sample. The presence of WIP mRNA is indicative of WIP expression. Such a method can be used, for example, as a screen for normal or abnormal expression of WIP, which can be associated with a disease caused by the abnormal expression of WIP.

Alternatively, a method of detecting WIP in a sample can be accomplished using an antibody directed against WIP or a portion of WIP. Detection of specific binding to the antibody indicates the presence of WIP in the sample (e.g., ELISA). This could reflect a pathological state associated with WIP or a deficiency of WIP, and thus, can be used diagnostically.

The sample for use in the methods of the present invention includes a suitable sample from, for example, a mammal, particularly a human. For example, the sample can be blood (e.g., PMBC), tissue and lymph and/or urine.

The WIP sequences of the present invention can also be used to generate nonhuman gene knockout animals, such as mice, which lack WIP and transgenically overexpress WIP. For example, such WIP gene knockout mice can be generated and used to obtain further insight into the function of WIP as well as assess the specificity of WIP activators and inhibitors. Also, overexpression of WIP (e.g., human WIP) in transgenic mice can be used as a means of creating a test system for WIP activators and inhibitors (e.g., against human WIP). In addition, the WIP gene can be used to clone the WIP promoter/enhancer in order to identify regulators of WIP transcription. WIP gene knockout animals include animals which completely or partially lack the WIP gene and/or WIP activity or function.

The present invention is illustrated by the following examples, which are not intended to be limiting in any way.

EXAMPLES

Materials and Methods

The materials and methods described below were used in the Examples which follow.

Molecular Cloning of WIP Using Yeast Two Hybrid System

Full length WASP cDNA, obtained by reverse transcription polymerase chain reaction (RT-PCR) from peripheral blood T cells, sequence verified, cloned into the bait vector pGBT9 (Clontech, Palo Alto, Calif.) was used to screen a cDNA library constructed from the human lymphoma T cell line KT3 in the activation domain vector pGAD424 (Wright, D. A., Futcher, B., Ghosh, P. & Geha, R. S. (1996) *J. Biol. Chem.*, 271: 31037–31043). Double transformants were selected on Leu⁻, Trp⁻, His⁻ plates containing 20 mM aminotriazole to suppress non-specific background.

Rapid Amplification of cDNA Ends (RACE)

The 5' end of WIP cDNA was obtained by RACE. Two nested antisense primers corresponding to nucleotides 487–510 (5'-GCGGCATTCGGTTCCTCTGAGGCT (SEQ ID NO: 15), WIP-out) and 452–476 (5'-ACTTCTGTGGCCTGGAGAAGGCACA (SEQ ID NO: 16), WIP-in) of the WIP cDNA were constructed and used to PCR a RACE ready library from human peripheral blood mononuclear cells (PBMC) (Marathon library, Clontech, Palo Alto, Calif.) along with the anchor primers supplied by the vendor and LA Taq enzyme (Panvera, Milwaukee, Wis.). The PCR parameters were as follows: denaturation at 94° C. for 30 seconds, annealing at 65° C. for 1 minute, and extension at 68° C. for 4 minutes. Five independent clones derived from three independent PCR reactions were sequenced to verify the sequence of WIP cDNA. Sequence analysis was performed using the GCG version 8.1 package (Genetics Computer Group). The BLAST and the FASTA programs were used to search the GenBank databases at the National Center for Biotechnology Information (NCBI).

Northern Blot Analysis of WIP mRNA Expression

Human multiple tissue Northern blots were purchased from Clontech (Palo Alto, Calif.). After overnight hybridization with radiolabeled full length WIP cDNA, the blots were washed with 0.5×SSC containing 0.1% SDS at 65° C. for 1 hour with two changes of buffer, dried and autoradiographed.

Multiple tissue Northern blots containing 2 mg of human mRNA per lane were hybridized with $^{32}$P labeled full length WIP cDNA probe. The filter was exposed for 12 hr. As a control for loading, the blot was reprobed for GAPDH transcript.

Glutathione S-Transferase (GST) and Maltose Binding Protein (MBP) Fusion Proteins To obtain the GST-WASP$_{1-270}$ construct, cDNA coding for amino acids (a.a.) 1-270 of WASP was amplified by PCR using Pfu polymerase (Stratagene, San Diego, Calif.) and oligonucleotides with EcoRI (5' end) or Sal I (3' end) recognition sequence and cloned into EcoRI-Sal I digested pGEX4T1 (Pharmacia, Piscataway, N.J.). MBP fusion construct of WIP 4 (MBP-WIP4) was made by ligating WIP4 (a clone of WIP obtained by two hybrid screen, see results) cDNA excised from pGAD424 by digestion with EcoRI and Bgl II to EcoRI-Bam HI digested pMAL-c2 expression vector (New England Biolabs, Beverly, Mass.). GST-WIP2 construct was made by ligating WIP2 cDNA excised from the yeast vector pGAD424 by EcoRI-Bgl II digestion to EcoRI-Bam HI digested pGEX4T1. All expression constructs were verified by DNA sequence analysis, and transformed into *E. coli* BL21 for the expression of the fusion proteins.

WASP$_{1-270}$, WIP4 and the control protein M were expressed in *E. coli* as fusion proteins with GST or MBP. Soluble extracts from induced bacteria were mixed and the fusion proteins were affinity precipitated using GSH beads, or amylose resin, run on 4–15% gradient SDS-PAGE and examined for the presence of MBP fusion proteins by Western blotting with rabbit anti-MBP antiserum. The blots were developed using protein A conjugated to horseradish peroxidase followed by ECL. The molecular weight of MBP-WIP and of the control MBP-M proteins were similar. The lower molecular bands represented degradation products of the fusion proteins. The presence of GST-WASP$_{1-270}$ and of GST was confirmed by Western blotting with anti-GST mAb.

Expression of fusion proteins was induced as follows: GST-WASP$_{1-270}$ expression was induced for 2 hours with 0.075 mM isopropyl-thio-β-D-galactopyranoside (IPTG). After induction, the bacterial cells were collected by centrifugation, suspended in GST-lysis buffer (20 mM Tris pH 8.0, 150 MM NaCl, 1 mM EDTA, 1 mM DTT, 0.5% NonidetP-40, protease inhibitor mixture (Complete, Boehringer Mannheim, Indianapolis, Ind.) and 0.1% lysozyme) and lysed by sonication (3×15 second). The lysate was clarified by centrifugation at 10,000×g for 5 minutes at 4° C. GST expression was induced by addition of 0.1 mM IPTG and the cells were processed as above.

MBP-WIP4 was induced with 0.3 mM IPTG for 16 hours at 30° C. MBP-M was induced with 0.3 mM IPTG for 2 hours at 37° C. Bacteria were collected by centrifugation and suspended in 1/20 growth volume in *E. coli* lysis buffer (20 mM Tris, pH 7.4, 200 mM NaCl, 1 mM EDTA with protease inhibitors) and frozen at −20° C. for 2 hours. The suspensions were thawed, sonicated (3×15 sec), and centrifuged for 20 minutes at 10,000×g and 4° C. The supernatants were used in affinity precipitation experiments.

Lysates of BJAB cells were incubated with GSH-Sepharose beads coupled to GST-WIP2 or GST. Bound proteins were eluted, run on 10% SDS-PAGE and examined for the presence of WASP by immunoblotting with rabbit anti-WASP peptide antibody. The blots were developed as described above.

Expression of FLAG-WIP4 protein in clone I was demonstrated by the presence of a specific band corresponding to FLAG-WIP4 in immunoblots of anti-FLAG immunoprecipitates developed with anti-FLAG mAB followed by peroxidase labeled goat anti-mouse Ig and ECL. This band was absent in the control clone A.11 transfected with pcDNA3 alone. The heavy (H) and light (L) chains of the immunoprecipitating mAb were visualized. Full length FLAG-WIP did not transfer in immunoblotting. Expression of FLAG-WIP protein in clone 3 transfected with FLAG-WIP was inferred by the presence of a specific band corresponding to WASP in immunoblots of anti-FLAG immunoprecipitate developed with rabbit anti-WASP followed by protein A and ECL. This band was absent in the control clone A.11.

In vitro Binding Assay Using GST and MBP Fusion Proteins

Supernatant of bacterial cell lysates containing GST or GST-WASP$_{1-270}$ fusion protein was mixed with supernatant of bacterial cell lysates containing MBP-WIP4 or MBP-M for 20 minutes at 4° C. One half of the mixture was tumbled with glutathione (GSH)-beads and the other with amylose resin at 4° C. for 40 minutes. The beads were washed thrice with tris-buffered saline containing 0.5% Tween 20, and the beads were suspended in 1× Laemmli PAGE buffer and subjected to Western blot analysis.

Generation of WIP Expressing BJAB Cells

WIP and WIP4 cDNAs were cloned into modified pcDNA3 vector that expresses cloned cDNA as a N-terminal FLAG fusion protein (gift of Dr. V. Ramesh, Massachusetts General Hospital, Boston, Mass.). Twenty μg of plasmid were used to transfect 30×10⁶ BJAB cells by electroporation (1600 μF, 200 V) and cells were selected in medium containing 1.5 mg/ml G418 (GIBCO-BRL, Rockville, Md.). The surviving cells were cloned by plating at 0.3 cells/well in a 96 well plate. The clones were checked for WIP4 expression by Western blotting with anti-FLAG. Because full length WIP-FLAG did not transfer for immunoblotting, expression of WIP-FLAG was ascertained by PCR and by the presence of WASP in anti-FLAG immunoprecipitates.

Affinity Precipitation of WASP and Profilin From Cell Lysates by WIP

BJAB cells were washed twice with serum free RPMI 1640 medium and suspended on ice for 30 minutes in lysis buffer (50 mM Tris pH 7.4, 150 mM NaCl, 1 nM EDTA, 30% glycerol, 0.4 mM sodium orthovanadate, 10 mM NaF, 10 mM sodium pyrophosphate, protease inhibitor cocktail and 1% Brij 96, Sigma, St. Louis, Mo.) at 40×10⁶ cells/ml. Lysates were centrifuged at 16,000×g for 15 min. at 4° C. and precleared for 1 hour with 25 μl of GST-Sepharose (Pharmacia). Supernatants were tumbled for 16 hours with ~1 μg of GST-WIP2 immobilized on GSH beads. The beads were washed 3 times with modified lysis buffer containing 10% glycerol and 0.2% Brij 96 (wash buffer), suspended in Laemmli loading buffer and subjected to PAGE on 10% (WASP) or 4–15% (profilin) gradient gels and Western blotting. The blots were developed with rabbit anti-WASP peptide antiserum and protein A-horseradish peroxidase (HRP) or with anti-profilin rabbit antibody.

Immunoprecipitation of FLAG-WIP From BJAB Cells.

FLAG-tagged full length WIP cDNA was transfected into BJAB cells and the cell lysates were immunoprecipitated with M2 anti-FLAG mAb, blotted and probed with anti-WASP peptide antibody.

BJAB cells transfected with WIP or with pcDNA3 vector were washed twice with serum free RPMI 1640 medium and lysed (40×10⁶ cells/ml) in ice-cold lysis buffer (10 mM Tris pH 7.4, 150 mM NaCl, 1 mM EDTA, 1% Triton X-100, 1% sodium deoxycholate, 0.1% SDS, 1 mM sodium orthovanadate, 50 mM NaF, and 1 mM phenylmethylsulfonylfluoride). The lysates were incubated at 4° C. overnight with 7 μg of anti-FLAG M2 antibody (Kodak-IBI) preadsorbed onto 40 μl of protein G Sepharose (Pharmacia, Piscataway, N.J.). The precipitates were washed 4× with wash buffer, eluted in Laemmli loading buffer and subjected to SDS-PAGE on 4–15% gradient gels and Western blot analysis with anti-FLAG mAb or anti-WASP antiserum.

Determination of Polymerized Actin Content

F-actin content was estimated by flow cytometry using fluorescein isothiocyanate (FITC)-phalloidin (Hartwig, J. H., Bokoch, G. M., Carpenter, C. L., Janmey, P. A., Taylor, L. A., Toker, A. & Stossel, T. P. (1995) *Cell*, 82: 643–653). The fluorescence of FITC-phalloidin in this assay is proportional to the amount of F-actin. Cells were fixed with 2% paraformaldehyde, perneabilized with 0.1% Triton X-100 and labeled with FITC-phalloidin for 30 min. at room temperature. The samples were immediately read in a Becton-Dickinson Excalibur flow cytometer. The samples were gated for live lymphocytes according to forward and side scatter profiles.

Untransfected cells (control), a pcDNA3 transfected clone (A.11) and representative clones expressing WIP (clone 3) and WIP4 (clone I) were permeabilized, stained with rhodamine-conjugated phalloidin and examined by immunofluorescence microscopy.

Immunofluorescence Microscopy

Cells were fixed with 3.7% paraformaldehyde in PBS at room temperature for 30 minutes, washed twice with PBS and permeabilized with 0.1% Triton X-100 in PBS at room temperature for 20 minutes. The cells were incubated with 2 μM tetramethylrhodamine B isothiocyanate (TRITC) conjugated phalloidin (Sigma, St. Louis, Mo.) for 1 hour at 37° C. The cells were washed twice with PBS, examined and photographed in a fluorescent microscope (Olympus).

Example 1

Molecular Cloning of WIP

The yeast two hybrid system was used to search for novel WASP interacting protein(s). A cDNA library from the human lymphoma T cell line KT3 was constructed in the activation domain vector pGAD424 (17 Wright, D. A., Futcher, B., Ghosh, P. & Geha, R. S. (1996) *J. Biol. Chem.*, 271: 31037–31043) and was screened in the yeast two-hybrid system using full length WASP cDNA. Six clones that grew on Leu⁻ Trp⁻ His⁻ plates also tested positive for β-galactosidase with blue color developing in less than 30 minutes. The two largest cDNAs, designated WIP2 (1.7 kb) and WIP4 (1.6 kb), were chosen for further detailed characterization. DNA sequence analysis revealed that WIP2 and WIP4 cDNAs are products of the same gene because the WIP4 protein coding sequence was completely contained within WIP2 (FIG. 1C). The 3'-untranslated region of WIP4 was 0.5 kb larger than that of WIP2. Genebank database search revealed that WIP is virtually identical to Prp12, a partial human cDNA isolated from tonsillar B cells whose function is unknown (accession number X86019). The last seven amino acids (a.a.) of the predicted Prp12 protein are replaced in WIP by seventeen a.a. of a different sequence (FIG. 1C). In addition, there is a deletion of one a.a. (a.a. 270 of the Prp12 sequence). Both of these differences are unlikely to be cloning artifacts since they are found in both WIP2 and WIP4 which were isolated during independent screenings. The 5' end of the WIP mRNA was obtained by RACE, using a peripheral blood leukocyte cDNA library. FIG. 1D shows the deduced a.a. sequence of WIP. The predicted protein product is a 503 a.a. long proline-rich protein with a calculated molecular weight of ~52 kD. The N-terminal region contains two stretches, 28 and 17 a.a. residues in length, that are highly homologous to corresponding a.a. stretches in the N-terminal region of the yeast protein verprolin (FIG. 1E). Verprolin is involved in cytoskeletal organization because vrp1⁻ conditional mutants fail to grow at the restrictive temperature of 37° C., have abnormal actin formation and chitin deposition and are defective in bud formation (19 Donnelly, S. F. H., Pocklington, M. J., Pallotta, D. & Orr, E. (1993) *Mol. Microbiol.*, 10: 585–596).

Of note is the presence of the KLKK (SEQ ID NO: 4) motif in the first WIP verprolin homology domain. This motif was originally identified in thymosin-β4 as a motif which is critical for actin binding (van Troys, M., Dewitte, D., Goethas, M., Carlier, M. F., Vanderkerckhove, J. & Ampe, C. (1 996) *EMBO J.*, 15: 201–210.21). Identical, or similar (KLRK (SEQ ID NO: 17), KLRR (SEQ ID NO: 18)), motifs are present in the putative actin binding protein members of the Ena/VASP family (Gertler, F. B., Niebuhr, K., Reinhard, M., Wehiand, J. & Soriano, P. (1996) *Cell*, 87: 227–239), raising the possibility that WIP may interact directly with actin. In addition, WIP contains two APPPPP (SEQ ID NO: 19) sequences (denoted by asterisk in FIG. 1D) which have been shown to bind profilin (Purich, D. L. and Southwick, F. S. (1997) *Biochem. Biophys. Res. Comm.*, 231:686–691), a protein that regulates actin polymerization.

WIP contains a number of putative SH3 binding motifs with the sequence PPPΨXP (SEQ ID NO: 20). A unique proline rich motif, GRSGPXPPXP (SEQ ID NO: 7) is repeated three times in WIP (FIG. 1F). This motif recurs twice in WASP and has been implicated in the binding of WASP to the SH3 domain containing proteins fyn, fgr and phospholipase Cγ1 (Finan, P. M., Soames, C. J., Wilson, L., Nelson, D. L., Stewart, D. M., Truong, O., Hsuan, J. J. & Kellie, S. (1996) *J. Biol. Chem.*, 271: 26291–26295). The presence of conserved SH3 binding motifs in WIP suggests that WIP may link the signal transduction machinery to the cytoskeleton.

Example 2

WIP Associates With WASP Both in vitro and in vivo.

The association of WASP and WIP was confirmed by several experiments. First, the interaction of WASP and WIP expressed as recombinant bacterial fusion proteins with glutathione S transferase (GST) and maltose binding protein (MBP), respectively, was examined. GSH-Sepharose retained MBP-WIP following incubation with a mixture of MBP-WIP and GST-WASP, indicating binding of WIP to WASP and suggesting that posttranslational modification of these proteins is not necessary for their interaction. Endogenous WASP from the human B cell line BJAB was also shown to bind to purified recombinant GST-WIP2. More importantly, WIP and WASP were shown to associate in cells. A protein band corresponding to WASP was detected in anti-FLAG immunoprecipitates from BJAB cells transfected with full length FLAG-WIP cDNA, but not in anti-FLAG immunoprecipitates from cells transfected with empty vector. WASP was not detected in control MOPC21 (mouse IgG1) immunoprecipitates from FLAG-WIP transfected BJAB cells.

Figure 2B:
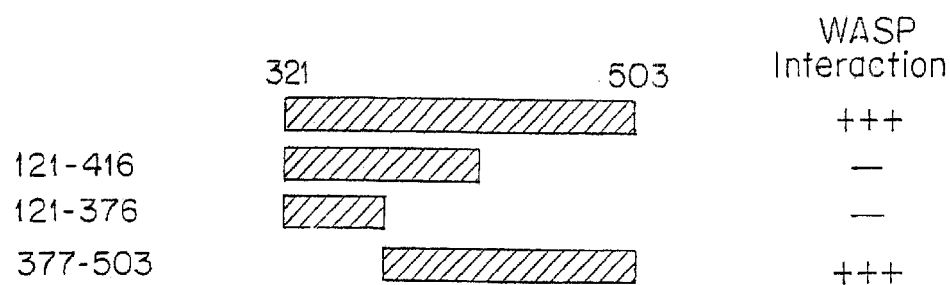
FIG. 2B is a map of the WASP binding site of WIP. Truncation mutants of WIP4 (a.a. 321–503), generated by cleavage with appropriate restriction enzymes were cloned into the pGAD424 vector and examined for WASP binding in the yeast two hybrid system. Interactions were scored as indicated above in FIG. 2A.

WASP binds to activated Cdc42 at a conserved GBD domain (a.a. 238–257) (Aspenstrom, P., Lindberg, U. & Hall, A. (1996) *Curr. Biol*, 6: 70–75; Kolluri, R., Tolias, K. F., Carpenter, C. L., Rosen, F. S. & Kirchhausen, T. (1996) *Proc. Natl. Acad. Sci. (USA)*, 93: 5615–5618; Symons, M., Derry, J. M. J., Kariak, B., Jiang, S., Lemahieu, V., McCormick, F., Francke, U. & Abo, A. (1996) *Cell*, 84: 723–734). To map the WIP binding site, truncations of WASP were examined for WIP binding in the yeast two hybrid system. The results show that the WIP binding region lies within the N-terminal 170 a.a. of WASP (FIG. 2A). Since this region lacks the GBD domain (a.a. 238–257), the WIP binding site on WASP is distinct from the Cdc42 binding site. Neither the WASP 1–137 truncation mutant which contains the WHI domain nor the proline-rich a.a. 139–270 region were able to bind WIP. Thus, both of these regions are necessary, but not sufficient, for WIP binding. Deletion of the N terminal 46 a.a., which disrupts the pleckstrin homology (PH) domain, but not the WH1 domain, sharply reduced the affinity of WASP for WIP suggesting that a.a. 1–46 are required for optimal binding to WIP. Curiously, the majority of point mutations in patients with WAS are located in the WH1 domain, although this domain makes up only 18% of the WASP sequence (Schwarz, K., Nonoyama, S., Peitsch, M., de Saint Basile, G., Espanol, T., Fasth, A., Fischer, A., Freitag, K., Friedrich, W., Fugmann, S., Hossle, H.-P., Jones, A., Kinon, C., Meindl, A., Notaranagelo, L., Weschler, A., Weiss, M. & Ochs, H. (1996) *Immunol. Today*, 17: 496–502). Mutations in the WH1 domain could potentially disrupt the association of WASP with WIP, raising the possibility that interaction of WASP with WIP may be critical for WASP function. The carboxy terminal 183 a.a. of WIP, i.e., WIP4 (a.a. 321–503), are sufficient for WASP binding. To further localize the binding site of WASP on WIP, truncation mutants of WIP4 were constructed and examined for binding to WASP in the yeast two hybrid system (FIG. 2B). The results show that the WASP binding region lies within a.a. 377–503 of WIP. Further analysis showed that the WASP binding region lies within amino acid residues 415 to 488.

Example 3

Assessment of Expression of WIP

The expression of WIP transcripts in human tissues was analyzed by Northern blot analysis of poly $A^+$ RNA from a panel of tissues using full length WIP cDNA as probe. Results showed that WIP is expressed in hematopoietic and non-hematopoietic tissues. Three species of mRNA with estimated sizes of 2.4 kb, 3.5 kb and 5 kb are present in all tissues tested. The different RNA species could represent a family of proteins or differently spliced/polyadenylated mRNA. Since the RNA bands are evident even when washed at relatively stringent conditions (0.5×SSC, 0.5% SDS), it suggests that the different bands are probably splice variants. The level of expression of the WIP transcripts is highest in PBMC, in which the 2.4 kb species is expressed at a higher level than the other two species. Expression of WIP in non-hematopoietic tissues, which do not express WASP, suggests that WIP may have other interaction partners than WASP.

Example 4

Expression of WIP Causes Actin Polymerization

WIP contains the highly charged KLKK (SEQ ID NO: 4) sequence (a.a. 45–48) in its N-terminal verprolin homology domain, immediately preceded by a region that could fold as an α-helix. This motif mediates contact between G-actin and thymosin β4 (van Troys, M., Dewitte, D., Goethas, M., Carlier, M. F., Vanderkerckhove, J. & Ampe, C. (1996) *EMBO J.*, 15: 201–210.21). WIP also contains two copies of the actin based motility sequence ABM-2, APPPPP (SEQ ID NO: 19), which has been implicated in binding to profilin in VASP and Mena (Gertler, F. B., Niebuhr, K., Reinhard, M., Wehland, J. & Soriano, P. (1996) *Cell*, 87: 227–239; Reinhard, M., Giehl, K., Abel, K., Haffner, C., Jarchau, T., Hoppe, V., Jockusch, B. M. & Walter, U. (1995) *EMBO J.*, 14. 1583–1589). One ofthe two profilin binding motifs in WIP (a.a. 8–13) is located in relative proximity to the G-actin binding motif as found in the Ena/VASP family of proteins. Simultaneous binding of G-actin and profilin by Ena/VASP is thought to promote actin polymerization (Gertler, F. B., et al., *Cell*, 87:227–239 (1996)). To examine the role of WIP on actin polymerization, the effect of overexpression of WIP on F-actin content was examined in B lymphocytes. FLAG-tagged full length WIP and FLAG-tagged WIP4 (a.a. 321–503) were cloned into pcDNA3 and transfected into BJAB cells. Transfected cells were selected using the antibiotic G418 and cloned. To ascertain the expression of FLAG-WIP proteins, cell lysates were immunoblotted with anti-FLAG mAb M2. The FLAG-WIP4 product was readily detectable in cell lysates and in immunoprecipitates with anti-FLAG M2 mAb. Despite multiple attempts using a number of immunoblotting conditions, the full length FLAG-WIP product could not be immunoblotted, possibly because of its very high proline content. However, for the representative clone 3, the presence of WASP was demonstrated in anti-FLAG immunoprecipitates from FLAG-WIP transfected cells, providing evidence for expression of tagged WIP protein that interacted with WASP. Expression of FLAG-WIP mRNA was also ascertained in several clones by RT-PCR.

F-actin content was assessed by staining permeabilized cells with FITC-conjugated phalloidin followed by flow cytometry analysis. Table 1 shows that there was an increase in baseline F-actin content in BJAB cell clones that overexpressed full length WIP, but not in control transfected cells. The effect of WIP overexpression on F-actin content was dependent on the N-terminal region of WIP. Overexpression of WIP4 which lacks the first 320 a.a. and thus lacks the actin binding KLKK (SEQ ID NO: 4) motif and one of two profilin binding ABM-2 sequences did not cause an increase in F-actin content.

TABLE 1

Effect of Overexpression of WIP on F-Actin Content in BJAB cells

| Transfection | Cells | Relative F-actin content |
| --- | --- | --- |
| Untransfected | BJAB | 1.0 |
| pcDNA3 | Clone A.11 | 0.96 ± 0.25 |
| FLAG-WIP | Clone 2 | 1.40 ± 0.25 |
|  | Clone 3 | 1.79 ± 0.11 |
|  | Clone 4 | 1.55 ± 0.01 |
| FLAG-WIP4 | Clone I | 1.10 ± 0.17 |

F-actin content was determined by measuring mean fluorescence intensity in permeabilized cells stained with FITC-phalloidin. The F-actin content represents the mean ratio of the F-actin content in transfected cells to that in untransfected BJAB cell in 4 experiments. t tests revealed that FLAG-WIP clones 2, 3 and 4 were significantly higher ($p \leq 0.001$). There was no significant difference between Clone A.11 and Clone I (p=0.20).

It was previously shown that overexpression of WASP causes the formation of cytosolic aggregates containing F-actin and WASP (Symons, M., Derry, J. M. J., Kariak, B., Jiang, S., Lemahieu, V., McCormick, F., Francke, U. & Abo, A. (1996) *Cell*, 84: 723–734). The effect of WIP overexpression on F-actin distribution was assessed by immunofluorescence microscopy of permeabilized BJAB cells stained with TRITC-phalloidin. Results showed that F-actin is uniformly distributed around the cortex in untransfected cells (control) and in cells transfected with pcDNA3. In contrast, in clone 3, which overexpresses full length FLAG-tagged WIP, the cell surface was covered with cerebriform projections containing actin. The cerebriform nature of the projections is reflected in the lacy staining pattern. Formation of surface projections and the increase in F-actin content were dependent on the N-terminal region of WIP, because F-actin staining in clones which overexpress WIP4 was indistinguishable from that of control cells.

Example 5

GST-WIP Affinity Precipitates Endogenous Profilin

In light of the capacity of WIP to increase F-actin content, the critical role of profilin in actin polymerization (Pantaloni, D. & Carlier, M.-F. (1993) *Cell*, 75: 1007–1014; Theriot, J. A. & Mitchison, T. J. (1993) *Cell*, 75: 835–838), and the presence of profilin binding motifs in WIP, the capacity of WIP to bind profilin was examined. Profilin was readily detected in lysates of BJAB cells by immunoblotting with rabbit anti-profilin antibody. GST-WIP2, but not GST, retained endogenous profilin following incubation with BJAB cell lysate.

Example 6

WIP Binds to Adaptor Protein Nck

Yeast Two-hybrid System—Full-length Nck cDNA was cloned in-frame into the bait vector pGBT9 (CLONTECH). The sequence of the clone was confirmed by DNA sequence analysis, and the clone was designated Nck-GBT9.

WIP4 is a truncation of WIP cDNA that encodes the carboxyl-terminal portion of WIP (amino acids 321–503) (Ramesh, N. A., et al., *Proc. Natl. Acad. Sci. USA*, 94:14671–14676 (1997)). WIP4 cDNA cloned in the yeast two-hybrid vector pGAD was used to construct the WIP4 deletion mutants. Deletions were obtained by digestion with the appropriate restriction enzymes followed by Klenow treatment and religation. pGAD-WIP-(321–415) was obtained by digestion with StuI and PstI, and pGAD-WIP-(321–376) was obtained by digestion with SfiI and PstI, and pGAD-(377–503) was obtained by SfiI digestion, Klenow treatment, EcoRI digestion, and a second Klenow treatment. WIP inserts for pGAD-WIP-(415–503) and pGAD-WIP-(416–488) constructs were obtained by polymerase chain reaction. All constructs were confirmed by sequencing.

Yeast transformation and colony analysis were performed according to the manufacturer's instructions (Matchmaker Two-Hybrid System Protocol, CLONTECH).

GSTFusion Proteins—Glutathione S-transferase (GST) fusion proteins of Nck and of each of its three SH3 domains were generated as described previously (Lu, W. et al., *Curr. Biol.*, 7:85–93 (1997)). All expression constructs were verified by DNA sequence analysis. Expression of fusion proteins in transformed *Escherichia coli* was induced for 2 h with 0.1 mM isopropyl-thio-β-D-galactopyranoside. Fusion proteins were purified as described previously (Ramesh, N. A., et al., *Proc. Natl. Acad. Sci. USA*, 94:14671–14676 (1997)).

Generation of WIP Expressing BJAB Cells—WIP4 cDNA was cloned into a modified pcDNA3 vector that expressed cloned cDNA as an amino-terminal FLAG fusion protein and was transfected into the human B lymphoma cell line BJAB as described (Ramesh, N. A., et al., *Proc. Nat. Acad. Sci. USA*, 94:14671–14676 (1997)). The culture medium for BJAB-transfected cells was supplemented with 1.5 mg/ml G418 (Calbiochem).

Affinity Precipitation of WIP by GST Fusion Proteins—Lysates of BJAB cells transfected with pcDNA3 or with pcDNA-WIP4 were obtained as described previously (Ramesh, N. A., et al., *Proc. Natl. Acad. Sci. USA*, 94:14671–14676 (1997)) and precleared for 1 h with 25 μl of GST-Sepharose (Amersham Pharmacia Biotech). Supernatants were tumbled for 16 h with 2 μg of GST or GST fusion proteins immobilized on GSH beads. The beads were washed, suspended in Laemmli loading buffer and subjected to PAGE on 4–15% gradient gels and Western blotting. The blots were developed with rabbit anti-WIP followed by protein A conjugated to horseradish peroxidase or with anti-FLAG M2 mAb followed by goat anti-mouse conjugated to horseradish peroxidase and enhanced chemiluminescent detection (ECL).

Immunoprecipitation of FLAG-WIP from BJAB Cells—BJAB cells or BJAB cells transfected with pcDNA-WIP were washed twice with phosphate-buffered saline and lysed ($46 \times 10^6$ cells in 0.35 ml) in ice-cold lysis buffer (50 mM Tris, pH 7.4, containing 150 mM NaCl, 5 mM $MgCl_2$, 30% glycerol, 0.4 mM $Na_3VO_4$, 10 mM NaF, 10 mM $Na_3P_2O_7$, protease inhibitor mixture (Complete, Boehringer Mannheim) and 1% Brij 96) for 30 min. Lysates were centrifuged at 16,000×g for 15 min at 4° C. and precleared for 1 h at 4° C. with 5 μl of normal mouse serum bound to protein G-Sepharose (Amersham Pharmacia Biotech) and then incubated overnight at 4° C. with 8 μg of anti-FLAG M2 monoclonal antibody (mAb) or of isotype-matched control MOPC21 mAb preadsorbed onto 40 μl of protein G-Sepharose. The precipitates were washed 4× with modified lysis buffer containing 10% glycerol and 0.2% Brij-95, eluted in Laemmli loading buffer, and subjected to SDS-PAGE on 4–15% gradient gels and Western blot analysis with anti-FLAG mAb or anti-Nck mAb (Transduction Laboratories). The blots were developed by ECL as described above.

RESULTS AND DISCUSSION

Nck Interacts with WIP in the Yeast Two-Hybrid System—WIP contains several proline-rich sequences including three repeats of the sequence GRSGPXPPXP (SEQ ID NO: 7). This sequence is repeated twice in WASP and is involved in the binding of WASP to the SH3.3 domain of Nck (Finan, P. M. et al., *J. Biol. Chem.*, 271:26291–26295 (1996)). Therefore, it is likely that WIP may be a candidate for binding to Nck. Since all the three GRSGPXPPXP (SEQ ID NO: 7) sequences were present within WIP4, a truncation of WIP that contains amino acids 321–503, the interaction of WIP4 with Nck by the yeast two-hybrid system was tested. Table 2 shows that Nck interacts specifically with WIP4. Nck did not interact with human TRAF1 (tumor necrosis factor receptor-associated factor 1) used as a control, and WIP4 did not with laminin (Table 2). As expected, WIP4 interacted with WASP (Ramesh, N. A., et al., *Proc. Nati. Acad. Sci. USA*, 94:14671–14676 (1997)).

TABLE 2

Interaction of Nck and WJP by the yeast two-hybrid system
Two-hybrid assay results for HF7c clones containing the Gal
4 binding (pGBT9) or activation (pGAD424) domain vectors
with the indicated fusion protein insert are shown.
WIP4 represents amino acids 321–503 of WIP. TRAF1
represents amino acids 62–416 of human TRAF1.
A − indicates no growth on Leu/Trp/His negative
SD synthetic medium in the presence of 20 mM S-aminotriazole.
++ denotes growth both on the selective medium and
β-galactosidase activity with color development in 2 h,
+++ indicates growth on the selective medium
and color change in 30 min. ND, not done.

| | | pGAD424 | |
|---|---|---|---|
| pGBT9 | None | WIP4 | TRAF1 |
| None | ND | − | − |
| Nck | − | ++ | − |
| WASP | − | +++ | − |
| Laminin | − | − | ND |

Endogenous Nck Co-immunoprecipitates with WIP from BJAB Cells—To demonstrate the Nck-WIP associated in vivo, whether Nck and WIP co-immunoprecipitate from cells was examined. To this purpose, the presence of Nck in anti-FLAG immunoprecipitates of lysates from human B cells BJAB transfected with FLAG-tagged WIP4 cloned in pcDNA3 was examined.

Nck was present in anti-FLAG immunoprecipitates from FLAG-WIP4 transfected cells. Nck was not detected in MOPC21 mAb immunoprecipitates of WIP4-transfected cells nor in M2 immunoprecipitates of untransfected BJAB cells. To ascertain the presence of FLAG-tagged WIP in the immunoprecipitates, the membrane was stripped and reblotted with anti-FLAG M2 mAb. FLAG-tagged WIP4 is detected in M2 immunoprecipitates from BJAB cells transfected with FLAG-WIP4 and, as expected, in total lysates from FLAG-WIP4-transfected cells. FLAG-WIP4 was neither detected in MOPC21 immunoprecipitates from WIP4-transfected cells nor in M2 immunoprecipitates from untransfected cells.

Treatment of cells with phorbol 12-myristate 13-acetate for 15, 30, or 60 minutes did not alter the capacity of Nck and WIP to co-immunoprecipitate suggesting that Nck phosphorylation induced by phorbol 12-myristate 13-acetate (Park, D. and Rhee, B. G., *Mol. Cell. Biol.*, 12:5816–5823 (1992)) does not regulate WIP-Nck interaction.

WIP Binds to the Second SH3 Domain of Nck—To confirm Nck interaction with full-length WIP, GST-Nck fusion protein was used to affinity precipitate endogenous WIP from BJAB cells. The precipitates were run on SDS-PAGE and Western-blotted with anti-WIP rabbit antibody. WIP was present in GST-Nck precipitates but not in control GST precipitates.

Since proteins that bind to Nck have a preference for one of its three SH3 domains, which of the three SH3 domains of Nck preferentially interacts with WIP was determined. GST fusion proteins of Nck and of each of its individual SH3 domains were used to affinity precipitate WIP from BJAB cells transfected with FLAG-tagged WIP4 or with empty pcDNA3 vector, and the precipitates were run on SDS-PAGE and Western-blotted with anti-FLAG M2 antibody. WIP bound to the SH3.2 domain of Nck but not to the SH3.1 and SH3.3 domains of Nck. No bands were detected in precipitates of lysates from BJAB cells transfected with empty vector. With longer exposures, WIP binding to SH3.1 and SH3.3 domains of Nck but not to GST was detected. As a control for fusion protein loading, the gels were stained with Coomassie Blue. The small differences in the amounts of fusion protein used (<2-fold) are unlikely to account for the difference in the ability of the Nck SH3 domains to bind WIP.

Two copies of the sequence GRSGPXPPXP (SEQ ID NO: 7) which has been implicated in the binding of WASP to SH3.3 of Nck are present in the shortest truncation of WIP that binds Nck (WIP-(321–415)). Yet WIP bound poorly to SH3.3 of Nck. This suggests that residues other than those in the above sequence determine binding to individual SH3 domains of Nck. The SH3.3 domain of Nck mediates its binding to the serine/threonine kinase CKI-γ2 (Lussier, G. and Larose, L., J. Biol. Chem., 372:2688–2694 (1997)).

Mapping of the Nck-binding Site of WIP—As discussed above, WASP binds to the carboxyl-terminal region of WIP, amino acids 377–503 (Ramesh, N. A., et al., Proc. Natl. Acad. Sci. USA, 94:14671–14676 (1997)). To determine whether the WASP- and Nck-binding sites on WIP overlap, the interaction of WIP deletion mutants with WASP and Nck was examined using the yeast two-hybrid system. WIP-(416–488) bound to WASP but not to Nck. In contrast, the WIP deletion mutated WIP-(321–415) binds to Nck but not to WASP. Taken together, these results show that the WASP and Nck binding domains of WIP differ.

Since WIP and WASP bind preferentially to distinct SH3 domains of Nck, Nck may simultaneously engage WIP and WASP, thereby increasing the local concentration of both proteins and enhancing their interaction. Since different domains of Nck bind to WIP and WASP, different sites on WASP bind to WIP and Nck, and different sites on WIP bind to Nck and WASP; it is likely that trimolecular complexes of Nck, WIP, and WASP exist in which each of the proteins could contact the two others.

WIP May Bridge Nck to Profilin and the Cytoskeleton—WIP interacts with profilin (Ramesh, N. A., et al., Proc. Nat. Acad. Sci. USA, 94:14671–14676 (1997)). The two profilin binding consensus sequences in WIP (APPPPP) (SEQ ID NO: 19) are located at positions 8–13 and 427–432 and are outside the Nck-binding (amino acids 321–415). This raised the possibility that WIP may couple Nck to profilin. Whether profilin co-precipitates with Nck was examined. Endogenous profilin from lysates of BJAB cells was bound to GST-Nck but not to GST. Nck lacks proline-rich sequences, including profilin binding consensus sequences (A, G, L or S followed by PPPPP) (SID NO: 21) (Purich, D. L. and Southwick, F. B., Biochem. Biophys. Res. Commun., 231:686–691 (1997)) and fails to interact with profilin in the yeast two-hybrid system (data not shown). These results suggests that the binding of profilin to Nck is indirect and is likely mediated by WIP.

The Drosophila homologue of Nck, Dock, has been shown to be involved in the photorecptor cell (R cell) axon guidance, suggesting that it plays a role in cytoskeletal reorganization (Garrity, P. A. et al., Cell, 85:639–650 (1996)). In addition to binding profilin, WIP contains the actin-binding KLKK sequence, and its overexpression increases the cell content of F-actin. Furthermore, via its interaction with WASP (Ramesh, N. A., et al., Proc. Natl. Acad. Sci. USA, 94:14671–14676 (1997)) and N-WASP[3], WIP may modulate cytoskeletal reorganization. Therefore, it is likely that WIP links Nck to the actin cytoskeleton. Since Nck is recruited to RTKs following their tyrosine phosphorylation subsequent to ligand binding, the Nck-WIP interaction provides an important link between extracellular signaling via RTKs and reorganization of the cytoskeleton.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated nucleic acid which encodes WIP, a WASP-interacting protein comprising SEQ ID NO:1.

2. The nucleic acid of claim 1 wherein the nucleic acid encodes an amino acid sequence comprising SEQ ID NO:2.

3. An isolated fragment of SEQ ID NO:1 which encodes WIP, a WASP-interacting protein, wherein the fragment includes at least 10 consecutive nucleotides in the coding region of SEQ ID NO: 1 which are 5' of nucleotide 380 of SEQ ID NO: 1.

4. An isolated nucleic acid which encodes WIP, a WASP-interacting protein, and which selectively hybridizes under moderately stringent hybridization conditions to the complement strand of SEQ ID NO: 1, said moderately stringent hybridization conditions comprising washing with 0.5×SSC containing 0.1% SDS at 65° C. for 1 hour, and wherein said isolated nucleic acid comprises at least 10 consecutive nucleotides of the coding region of SEQ ID NO: 1 which are 5' of nucleotide 380 of SEQ ID NO: 1.

5. A recombinant nucleic acid construct comprising the nucleic acid of claim 1.

6. The recombinant nucleic acid construct of claim 5 wherein the nucleic acid encodes an amino acid sequence comprising SEQ ID NO: 2.

7. The recombinant nucleic acid construct of claim 5 wherein the nucleic acid is operably linked to an expression control sequence.

8. A host cell comprising the recombinant nucleic acid construct of claim 7.

9. The host cell of claim 8 wherein the nucleic acid is operably linked to an expression control sequence, whereby WIP is expressed when the host cell is maintained under conditions suitable for expression.

10. A method for producing a WASP-interacting protein comprising:

a) introducing into a host cell a nucleic acid construct comprising a nucleic acid comprising full length SEQ ID NO:1; and b) maintaining the host cell produced in step a) under conditions whereby the nucleic acid is expressed and the WASP-interacting protein is produced.

11. A isolated nucleic acid which encodes an amino acid sequence comprising SEQ ID NO:2.

12. A recombinant nucleic acid construct comprising the nucleic acid of claim 11.

13. The recombinant nucleic acid construct of claim 12, wherein the nucleic acid is operably linked to an expression control sequence.

14. A host cell comprising the recombinant nucleic acid construct of claim 13.

15. A method for producing a WIP polypeptide comprising culturing the host cell of claim 14 under conditions suitable for expression of the recombinant nucleic acid construct.

16. An isolated nucleic acid comprising of SEQ ID NO:1.

17. An isolated nucleic acid construct comprising the nucleic acid of claim 16.

18. The recombinant nucleic acid construct of claim 17, wherein the nucleic acid is operably linked to an expression control sequence.

19. A host cell comprising the nucleic acid construct of claim 18.

20. A method of producing a WIP polypeptide comprising culturing the host cell of claim 19 under conditions suitable for expression of the nucleic acid construct.

21. An isolated nucleic acid which encodes SEQ ID NO:2.

22. An isolated nucleic acid fragment of SEQ ID NO: 1, wherein the fragment includes at least 10 consecutive nucleotides in the coding region of SEQ ID: 1 which are 5' of nucleotide 380 of SEQ ID: 1.

23. An isolated fragment of SEQ ID NO: 1 which encodes WIP, a WASP-interacting protein, and which selectively hybridizes under moderately stringent hybridization conditions to the complement strand of SEQ ID NO: 1, said moderately stringent hybridization conditions comprising washing with 0.5×SSC containing 0.1% SDS at 65° C. for 1 hour, and wherein said isolated fragment comprises at least 10 consecutive nucleotides of the coding region of SEQ ID NO: 1 which are 5' of nucleotide 380 of SEQ ID NO: 1.

* * * * *

UNITED STATES PATENT AND TRADEMARK OFFICE
CERTIFICATE OF CORRECTION

PATENT NO.    : 6,635,446 B1
DATED         : October 21, 2003
INVENTOR(S)   : Narayanaswamy Ramesh et al.

It is certified that error appears in the above-identified patent and that said Letters Patent is hereby corrected as shown below:

<u>Column 47,</u>
Line 4, replace "A" with -- An --.
Line 20, delete "recombinant".

Signed and Sealed this

Tenth Day of February, 2004

JON W. DUDAS
*Acting Director of the United States Patent and Trademark Office*

SEQUENCE LISTING

<160> NUMBER OF SEQ ID NOS: 26

<210> SEQ ID NO 1
<211> LENGTH: 1698
<212> TYPE: DNA
<213> ORGANISM: Human
<220> FEATURE:
<221> NAME/KEY: CDS
<222> LOCATION: (1)...(1698)

<400> SEQUENCE: 1

```
ccc ggg cag gtt aga aga cag cag ggg aac tcg aga agt tgg ttg ttt      48
Pro Gly Gln Val Arg Arg Gln Gln Gly Asn Ser Arg Ser Trp Leu Phe
 1               5                  10                  15 tca gca gat taa aac aat aca gat tta tca gca aga ctg ttc aac gca      96
Ser Ala Asp  *  Asn Asn Thr Asp Leu Ser Ala Arg Leu Phe Asn Ala
                20                  25                  30 taa ctg ccc aag atg cct gtc cct ccc cct cca gca ccc ccg ccg ccc     144
 *  Leu Pro Lys Met Pro Val Pro Pro Pro Ala Pro Pro Pro Pro
                35                  40                  45 ccg acg ttt gca ctg gcc aat aca gag aag cct acc ttg aat aag aca     192
Pro Thr Phe Ala Leu Ala Asn Thr Glu Lys Pro Thr Leu Asn Lys Thr
            50                  55                  60
```

```
                                                              -continued gag cag gct ggg aga aat gct ctc ctt tct gat atc agc aaa ggg aag        240
Glu Gln Ala Gly Arg Asn Ala Leu Leu Ser Asp Ile Ser Lys Gly Lys
            65                  70                  75 aaa cta aag aag acg gtc acc aat gac aga agt gca cca ata ctg gac        288
Lys Leu Lys Lys Thr Val Thr Asn Asp Arg Ser Ala Pro Ile Leu Asp
 80                  85                  90 aaa cct aaa gga gct ggt gct gga ggc ggt ggt ggt ggc ttt ggt gga        336
Lys Pro Lys Gly Ala Gly Ala Gly Gly Gly Gly Gly Gly Phe Gly Gly
 95                 100                 105                 110 ggc ggc gga ttt ggc gga gga ggt ggt ggc gga ggc ggt gga agt ttt        384
Gly Gly Gly Phe Gly Gly Gly Gly Gly Gly Gly Gly Gly Gly Ser Phe
                115                 120                 125 gga ggg ggc gga cct cca ggt ctg gga gga ttg ttc cag gct gga atg        432
Gly Gly Gly Gly Pro Pro Gly Leu Gly Gly Leu Phe Gln Ala Gly Met
            130                 135                 140 ccg aag ctg aga tcc acc gcc aac agg gat aat gat tct gga gga agc        480
Pro Lys Leu Arg Ser Thr Ala Asn Arg Asp Asn Asp Ser Gly Gly Ser
                145                 150                 155 cga cca cca ttg ttg cca ccg gga gga aga tcc aca tct gcg aaa ccc        528
Arg Pro Pro Leu Leu Pro Pro Gly Gly Arg Ser Thr Ser Ala Lys Pro
160                 165                 170 ttt tca ccc cca agt ggc cca ggg agg ttt cct gtg cct tct cca ggc        576
Phe Ser Pro Pro Ser Gly Pro Gly Arg Phe Pro Val Pro Ser Pro Gly
175                 180                 185                 190 cac aga agt ggt ccc cca gag cct cag agg aac cga atg ccg ccc cca        624
His Arg Ser Gly Pro Pro Glu Pro Gln Arg Asn Arg Met Pro Pro Pro
                195                 200                 205 agg ccc gac gtg ggc tca aag cct gat agc att cct cct cca gta cct        672
Arg Pro Asp Val Gly Ser Lys Pro Asp Ser Ile Pro Pro Pro Val Pro
            210                 215                 220 agt act cca aga ccc att caa tca agt ctg cac aac cgg ggg tcc cca        720
Ser Thr Pro Arg Pro Ile Gln Ser Ser Leu His Asn Arg Gly Ser Pro
225                 230                 235 cca gtg ccc gga ggc ccc agg cag ccc agc ccc ggg ccc act cct ccc        768
Pro Val Pro Gly Gly Pro Arg Gln Pro Ser Pro Gly Pro Thr Pro Pro
240                 245                 250 cct ttc cct gga aac cgc ggc act gct ttg gga gga ggc tca ata cgt        816
Pro Phe Pro Gly Asn Arg Gly Thr Ala Leu Gly Gly Gly Ser Ile Arg
255                 260                 265                 270 cag tcc ccc ttg agc tcc tcc tcg ccc ttc tcc aac cgg cct ccc ctc        864
Gln Ser Pro Leu Ser Ser Ser Ser Pro Phe Ser Asn Arg Pro Pro Leu
                275                 280                 285 ccg cct acc ccc agc agg gcg ttg gat gac aaa ccc cct cca cca cct        912
Pro Pro Thr Pro Ser Arg Ala Leu Asp Asp Lys Pro Pro Pro Pro Pro
            290                 295                 300 cct cca gtg ggc aac agg ccc tcc atc cac agg gaa gcg gtt ccc cct        960
Pro Pro Val Gly Asn Arg Pro Ser Ile His Arg Glu Ala Val Pro Pro
305                 310                 315 cct cct cct cag aac aac aag cct cca gtg cct tcc act ccg cgg cct       1008
Pro Pro Pro Gln Asn Asn Lys Pro Pro Val Pro Ser Thr Pro Arg Pro
320                 325                 330 tcg gct cct cac agg ccc cac ctc cgc ccg cca cct ccc agc agg ccc       1056
Ser Ala Pro His Arg Pro His Leu Arg Pro Pro Pro Pro Ser Arg Pro
335                 340                 345                 350 ggg ccg cct cct ctg cct cca agt tcc agc ggc aat gac gaa acc cca       1104
Gly Pro Pro Pro Leu Pro Pro Ser Ser Ser Gly Asn Asp Glu Thr Pro
                355                 360                 365 aga ctc cca cag cgg aat ctg tcc ctc agt tcg tcc acg ccc ccg tta       1152
Arg Leu Pro Gln Arg Asn Leu Ser Leu Ser Ser Ser Thr Pro Pro Leu
            370                 375                 380
```

-continued

```
cct tcg cca gga cgt tca ggt cct ctt cct ccc cca gtg ccc agt gag    1200
Pro Ser Pro Gly Arg Ser Gly Pro Leu Pro Pro Pro Val Pro Ser Glu
        385                 390                 395 aga ccc cca cct cca gtg agg gac ccg cca ggc cga tca ggc ccc ctc    1248
Arg Pro Pro Pro Pro Val Arg Asp Pro Pro Gly Arg Ser Gly Pro Leu
    400                 405                 410 cca cca cct cct cca gta agc aga aac ggc agc aca tct cgg gcc ctg    1296
Pro Pro Pro Pro Pro Val Ser Arg Asn Gly Ser Thr Ser Arg Ala Leu
415                 420                 425                 430 cct gct acc cct cag ttg cca tcc agg agt gga gta gac agt ccc agg    1344
Pro Ala Thr Pro Gln Leu Pro Ser Arg Ser Gly Val Asp Ser Pro Arg
            435                 440                 445 agt gga ccc agg cct ccc ctt cct cct gat agg ccc agt gct ggg gca    1392
Ser Gly Pro Arg Pro Pro Leu Pro Pro Asp Arg Pro Ser Ala Gly Ala
        450                 455                 460 cct ccc cca cct cca cca tca aca tct att aga aat ggc ttc caa gac    1440
Pro Pro Pro Pro Pro Ser Thr Ser Ile Arg Asn Gly Phe Gln Asp
    465                 470                 475 tct cca tgt gaa gat gag tgg gaa agc aga ttc tac ttc cat ccg att    1488
Ser Pro Cys Glu Asp Glu Trp Glu Ser Arg Phe Tyr Phe His Pro Ile
480                 485                 490 tcc gat ttg cca cct cca gag cca tat gta caa acg acc aaa agt tat    1536
Ser Asp Leu Pro Pro Pro Glu Pro Tyr Val Gln Thr Thr Lys Ser Tyr
495                 500                 505                 510 ccc agc aaa ctg gca aga aac gaa agc cgg agt gga tcc aac cga aga    1584
Pro Ser Lys Leu Ala Arg Asn Glu Ser Arg Ser Gly Ser Asn Arg Arg
            515                 520                 525 gaa agg ggt ggt cca cca ctc cct ccc atc ccg agg tga tct ttg gct    1632
Glu Arg Gly Gly Pro Pro Leu Pro Pro Ile Pro Arg  *  Ser Leu Ala
        530                 535                     540 gct ctt ctc tac cca agc tca aga gct gct tct gtt ggt atc taa gaa    1680
Ala Leu Leu Tyr Pro Ser Ser Arg Ala Ala Ser Val Gly Ile  *  Glu
    545                 550                 555 ctg gat acc ctc ccc cct                                             1698
Leu Asp Thr Leu Pro Pro
    560

<210> SEQ ID NO 2
<211> LENGTH: 503
<212> TYPE: PRT
<213> ORGANISM: Human

<400> SEQUENCE: 2

Met Pro Val Pro Pro Pro Ala Pro Pro Pro Pro Thr Phe Ala
 1               5                  10                  15

Leu Ala Asn Thr Glu Lys Pro Thr Leu Asn Lys Thr Glu Gln Ala Gly
                20                  25                  30

Arg Asn Ala Leu Leu Ser Asp Ile Ser Lys Gly Lys Lys Leu Lys Lys
            35                  40                  45

Thr Val Thr Asn Asp Arg Ser Ala Pro Ile Leu Asp Lys Pro Lys Gly
        50                  55                  60

Ala Gly Ala Gly Gly Gly Gly Gly Phe Gly Gly Gly Gly Phe
65                  70                  75                  80

Gly Gly Gly Gly Gly Gly Gly Gly Gly Ser Phe Gly Gly Gly
                85                  90                  95

Pro Pro Gly Leu Gly Gly Leu Phe Gln Ala Gly Met Pro Lys Leu Arg
            100                 105                 110

Ser Thr Ala Asn Arg Asp Asn Asp Ser Gly Gly Ser Arg Pro Pro Leu
```

-continued

```
                115                 120                 125
Leu Pro Pro Gly Gly Arg Ser Thr Ser Ala Lys Pro Phe Ser Pro Pro
130                 135                 140

Ser Gly Pro Gly Arg Phe Pro Val Pro Ser Pro Gly His Arg Ser Gly
145                 150                 155                 160

Pro Pro Glu Pro Gln Arg Asn Arg Met Pro Pro Arg Pro Asp Val
                165                 170                 175

Gly Ser Lys Pro Asp Ser Ile Pro Pro Val Pro Ser Thr Pro Arg
                180                 185                 190

Pro Ile Gln Ser Ser Leu His Asn Arg Gly Ser Pro Val Pro Gly
                195                 200                 205

Gly Pro Arg Gln Pro Ser Pro Gly Pro Thr Pro Pro Phe Pro Gly
210                 215                 220

Asn Arg Gly Thr Ala Leu Gly Gly Ser Ile Arg Gln Ser Pro Leu
225                 230                 235                 240

Ser Ser Ser Ser Pro Phe Ser Asn Arg Pro Pro Leu Pro Pro Thr Pro
                245                 250                 255

Ser Arg Ala Leu Asp Asp Lys Pro Pro Pro Pro Pro Val Gly
                260                 265                 270

Asn Arg Pro Ser Ile His Arg Glu Ala Val Pro Pro Pro Pro Gln
                275                 280                 285

Asn Asn Lys Pro Pro Val Pro Ser Thr Pro Arg Pro Ser Ala Pro His
290                 295                 300

Arg Pro His Leu Arg Pro Pro Pro Ser Arg Pro Gly Pro Pro Pro
305                 310                 315                 320

Leu Pro Pro Ser Ser Ser Gly Asn Asp Glu Thr Pro Arg Leu Pro Gln
                325                 330                 335

Arg Asn Leu Ser Leu Ser Ser Ser Thr Pro Leu Pro Ser Pro Gly
                340                 345                 350

Arg Ser Gly Pro Leu Pro Pro Pro Ser Glu Arg Pro Pro Pro
                355                 360                 365

Val Arg Asp Pro Pro Gly Arg Ser Gly Pro Leu Pro Pro Pro Pro
370                 375                 380

Val Ser Arg Asn Gly Ser Thr Ser Arg Ala Leu Pro Ala Thr Pro Gln
385                 390                 395                 400

Leu Pro Ser Arg Ser Gly Val Asp Ser Pro Arg Ser Gly Pro Arg Pro
                405                 410                 415

Pro Leu Pro Pro Asp Arg Pro Ser Ala Gly Ala Pro Pro Pro Pro
                420                 425                 430

Pro Ser Thr Ser Ile Arg Asn Gly Phe Gln Asp Ser Pro Cys Glu Asp
                435                 440                 445

Glu Trp Glu Ser Arg Phe Tyr Phe His Pro Ile Ser Asp Leu Pro Pro
450                 455                 460

Pro Glu Pro Tyr Val Gln Thr Thr Lys Ser Tyr Pro Ser Lys Leu Ala
465                 470                 475                 480

Arg Asn Glu Ser Arg Ser Gly Ser Asn Arg Arg Glu Arg Gly Gly Pro
                485                 490                 495

Pro Leu Pro Pro Ile Pro Arg
                500

<210> SEQ ID NO 3
<211> LENGTH: 6
<212> TYPE: PRT
<213> ORGANISM: unknown
```

-continued

```
<220> FEATURE:
<223> OTHER INFORMATION: profilin motif

<400> SEQUENCE: 3

Ala Pro Pro Pro Pro Pro
 1               5

<210> SEQ ID NO 4
<211> LENGTH: 4
<212> TYPE: PRT
<213> ORGANISM: unknown
<220> FEATURE:
<223> OTHER INFORMATION: actin-binding motif

<400> SEQUENCE: 4

Lys Leu Lys Lys
 1

<210> SEQ ID NO 5
<211> LENGTH: 112
<212> TYPE: PRT
<213> ORGANISM: unknown
<220> FEATURE:
<223> OTHER INFORMATION: N-terminal of WIP, human

<400> SEQUENCE: 5

Met Pro Val Pro Pro Pro Ala Pro Pro Pro Pro Thr Phe Ala
 1               5                  10                  15

Leu Ala Asn Thr Glu Lys Pro Thr Leu Asn Lys Thr Glu Gln Ala Gly
                20                  25                  30

Arg Asn Ala Leu Leu Ser Asp Ile Ser Lys Gly Lys Lys Leu Lys Lys
             35                  40                  45

Thr Val Thr Asn Asp Arg Ser Ala Pro Ile Leu Asp Lys Pro Lys Gly
         50                  55                  60

Ala Gly Ala Gly Gly Gly Gly Gly Phe Gly Gly Gly Gly Phe
 65                  70                  75                  80

Gly Gly Gly Gly Gly Gly Gly Gly Gly Ser Phe Gly Gly Gly
                 85                  90                  95

Pro Pro Gly Leu Gly Gly Leu Phe Gln Ala Gly Met Pro Lys Leu Arg
            100                 105                 110

<210> SEQ ID NO 6
<211> LENGTH: 104
<212> TYPE: PRT
<213> ORGANISM: unknown
<220> FEATURE:
<223> OTHER INFORMATION: Saccharomyces cerevisiae, Verprolin N-terminal

<400> SEQUENCE: 6

Met Ala Gly Ala Pro Ala Pro Pro Pro Pro Pro Pro Ala Leu
 1               5                  10                  15

Gly Gly Ser Ala Pro Lys Pro Ala Lys Ser Val Met Gln Gly Arg Asp
                20                  25                  30

Ala Leu Leu Gly Asp Ile Arg Lys Gly Met Lys Leu Lys Lys Ala Glu
             35                  40                  45

Thr Asn Asp Arg Ser Ala Pro Ile Val Gly Gly Val Val Ser Ser
         50                  55                  60

Ala Ser Gly Ser Ser Gly Thr Val Ser Ser Lys Gly Pro Ser Met Ser
 65                  70                  75                  80

Ala Pro Pro Ile Pro Gly Met Gly Ala Pro Gln Leu Gly Asp Ile Leu
                 85                  90                  95
```

Ala Gly Gly Ile Pro Lys Leu Lys
            100

<210> SEQ ID NO 7
<211> LENGTH: 10
<212> TYPE: PRT
<213> ORGANISM: unknown
<220> FEATURE:
<223> OTHER INFORMATION: consensus sequence GRSGPXPPXP
<221> NAME/KEY: VARIANT
<222> LOCATION: (1)...(10)
<223> OTHER INFORMATION: Xaa = Any Amino Acid

<400> SEQUENCE: 7

Gly Arg Ser Gly Pro Xaa Pro Pro Xaa Pro
1               5                   10

<210> SEQ ID NO 8
<211> LENGTH: 10
<212> TYPE: PRT
<213> ORGANISM: unknown
<220> FEATURE:
<223> OTHER INFORMATION: WIP sequence 352-361a.a., human

<400> SEQUENCE: 8

Gly Arg Ser Gly Pro Leu Pro Pro Pro Pro
1               5                   10

<210> SEQ ID NO 9
<211> LENGTH: 10
<212> TYPE: PRT
<213> ORGANISM: unknown
<220> FEATURE:
<223> OTHER INFORMATION: WIP sequence 374-383 a.a., human

<400> SEQUENCE: 9

Gly Arg Ser Gly Pro Leu Pro Pro Pro Pro
1               5                   10

<210> SEQ ID NO 10
<211> LENGTH: 10
<212> TYPE: PRT
<213> ORGANISM: unknown
<220> FEATURE:
<223> OTHER INFORMATION: WIP sequence 410-419 a.a., human

<400> SEQUENCE: 10

Pro Arg Ser Gly Pro Arg Pro Pro Leu Pro
1               5                   10

<210> SEQ ID NO 11
<211> LENGTH: 10
<212> TYPE: PRT
<213> ORGANISM: unknown
<220> FEATURE:
<223> OTHER INFORMATION: WASP sequence 338-347 a.a.

<400> SEQUENCE: 11

Gly Arg Ser Gly Pro Leu Pro Pro Val Pro
1               5                   10

<210> SEQ ID NO 12
<211> LENGTH: 10
<212> TYPE: PRT
<213> ORGANISM: unknown
<220> FEATURE:
<223> OTHER INFORMATION: WASP sequence 376-385 a.a.

<400> SEQUENCE: 12

Gly Arg Ser Gly Pro Leu Pro Pro Pro Pro
 1               5                  10

<210> SEQ ID NO 13
<211> LENGTH: 6
<212> TYPE: PRT
<213> ORGANISM: unknown
<220> FEATURE:
<223> OTHER INFORMATION: PPPPPP domain of WASP

<400> SEQUENCE: 13

Pro Pro Pro Pro Pro Pro
 1               5

<210> SEQ ID NO 14
<211> LENGTH: 6
<212> TYPE: PRT
<213> ORGANISM: unknown
<220> FEATURE:
<223> OTHER INFORMATION: ABM-2 motif
<221> NAME/KEY: VARIANT
<222> LOCATION: (1)...(6)
<223> OTHER INFORMATION: Xaa = Any Amino Acid

<400> SEQUENCE: 14

Xaa Pro Pro Pro Pro Pro
 1               5

<210> SEQ ID NO 15
<211> LENGTH: 24
<212> TYPE: DNA
<213> ORGANISM: unknown
<220> FEATURE:
<223> OTHER INFORMATION: WIP-out PCR primer sequence, human

<400> SEQUENCE: 15
gcggcattcg gttcctctga ggct                                          24

<210> SEQ ID NO 16
<211> LENGTH: 25
<212> TYPE: DNA
<213> ORGANISM: unknown
<220> FEATURE:
<223> OTHER INFORMATION: WIP-in PCR primer sequence, human

<400> SEQUENCE: 16
acttctgtgg cctggagaag gcaca                                         25

<210> SEQ ID NO 17
<211> LENGTH: 4
<212> TYPE: PRT
<213> ORGANISM: unknown
<220> FEATURE:
<223> OTHER INFORMATION: KLRK motif in Ena/VASP

<400> SEQUENCE: 17

Lys Leu Arg Lys
 1

<210> SEQ ID NO 18
<211> LENGTH: 4
<212> TYPE: PRT
<213> ORGANISM: unknown
<220> FEATURE:
<223> OTHER INFORMATION: KLRR motif in Ena/VASP

```
<400> SEQUENCE: 18

Lys Leu Arg Arg
 1

<210> SEQ ID NO 19
<211> LENGTH: 6
<212> TYPE: PRT
<213> ORGANISM: unknown
<220> FEATURE:
<223> OTHER INFORMATION: APPPPP motif, WIP

<400> SEQUENCE: 19

Ala Pro Pro Pro Pro Pro
 1               5

<210> SEQ ID NO 20
<211> LENGTH: 6
<212> TYPE: PRT
<213> ORGANISM: unknown
<220> FEATURE:
<223> OTHER INFORMATION: PPP(psi)XP putative SH3 binding motif
<221> NAME/KEY: VARIANT
<222> LOCATION: (1)...(6)
<223> OTHER INFORMATION: Xaa = Any Amino Acid

<400> SEQUENCE: 20

Pro Pro Pro Xaa Xaa Pro
 1               5

<210> SEQ ID NO 21
<211> LENGTH: 6
<212> TYPE: PRT
<213> ORGANISM: unknown
<220> FEATURE:
<223> OTHER INFORMATION: profilin-binding consensus sequence
<221> NAME/KEY: VARIANT
<222> LOCATION: (1)...(1)
<223> OTHER INFORMATION: Xaa = A, G, L or S

<400> SEQUENCE: 21

Xaa Pro Pro Pro Pro Pro
 1               5

<210> SEQ ID NO 22
<211> LENGTH: 19
<212> TYPE: PRT
<213> ORGANISM: Artificial Sequence
<220> FEATURE:
<223> OTHER INFORMATION: Translated WIP ORF No.1

<400> SEQUENCE: 22

Pro Gly Gln Val Arg Arg Gln Gln Gly Asn Ser Arg Ser Trp Leu Phe
 1               5                  10                  15

Ser Ala Asp

<210> SEQ ID NO 23
<211> LENGTH: 12
<212> TYPE: PRT
<213> ORGANISM: Artificial Sequence
<220> FEATURE:
<223> OTHER INFORMATION: Translated WIP ORF No. 2

<400> SEQUENCE: 23

Asn Asn Thr Asp Leu Ser Ala Arg Leu Phe Asn Ala
 1               5                  10
```

```
<210> SEQ ID NO 24
<211> LENGTH: 507
<212> TYPE: PRT
<213> ORGANISM: Artificial Sequence
<220> FEATURE:
<223> OTHER INFORMATION: Translated WIP ORF No. 3

<400> SEQUENCE: 24
```

Leu Pro Lys Met Pro Val Pro Pro Pro Ala Pro Pro Pro Pro
 1               5                  10                  15

Thr Phe Ala Leu Ala Asn Thr Glu Lys Pro Thr Leu Asn Lys Thr Glu
            20                  25                  30

Gln Ala Gly Arg Asn Ala Leu Leu Ser Asp Ile Ser Lys Gly Lys Lys
        35                  40                  45

Leu Lys Lys Thr Val Thr Asn Asp Arg Ser Ala Pro Ile Leu Asp Lys
 50                  55                  60

Pro Lys Gly Ala Gly Ala Gly Gly Gly Gly Gly Phe Gly Gly Gly
 65                  70                  75                  80

Gly Gly Phe Gly Gly Gly Gly Gly Gly Gly Gly Ser Phe Gly
                85                  90                  95

Gly Gly Gly Pro Pro Gly Leu Gly Gly Leu Phe Gln Ala Gly Met Pro
            100                 105                 110

Lys Leu Arg Ser Thr Ala Asn Arg Asp Asn Asp Ser Gly Gly Ser Arg
        115                 120                 125

Pro Pro Leu Leu Pro Pro Gly Arg Ser Thr Ser Ala Lys Pro Phe
130                 135                 140

Ser Pro Pro Ser Gly Pro Gly Arg Phe Pro Val Pro Ser Pro Gly His
145                 150                 155                 160

Arg Ser Gly Pro Pro Glu Pro Gln Arg Asn Arg Met Pro Pro Arg
                165                 170                 175

Pro Asp Val Gly Ser Lys Pro Asp Ser Ile Pro Pro Val Pro Ser
            180                 185                 190

Thr Pro Arg Pro Ile Gln Ser Ser Leu His Asn Arg Gly Ser Pro Pro
        195                 200                 205

Val Pro Gly Gly Pro Arg Gln Pro Ser Pro Gly Pro Thr Pro Pro Pro
    210                 215                 220

Phe Pro Gly Asn Arg Gly Thr Ala Leu Gly Gly Ser Ile Arg Gln
225                 230                 235                 240

Ser Pro Leu Ser Ser Ser Ser Pro Phe Ser Asn Arg Pro Pro Leu Pro
                245                 250                 255

Pro Thr Pro Ser Arg Ala Leu Asp Asp Lys Pro Pro Pro Pro Pro
            260                 265                 270

Pro Val Gly Asn Arg Pro Ser Ile His Arg Glu Ala Val Pro Pro
        275                 280                 285

Pro Pro Gln Asn Asn Lys Pro Pro Val Pro Ser Thr Pro Arg Pro Ser
    290                 295                 300

Ala Pro His Arg Pro His Leu Arg Pro Pro Pro Ser Arg Pro Gly
305                 310                 315                 320

Pro Pro Pro Leu Pro Pro Ser Ser Ser Gly Asn Asp Glu Thr Pro Arg
                325                 330                 335

Leu Pro Gln Arg Asn Leu Ser Leu Ser Ser Thr Pro Pro Leu Pro
            340                 345                 350

Ser Pro Gly Arg Ser Gly Pro Leu Pro Pro Val Pro Ser Glu Arg
        355                 360                 365

-continued

```
Pro Pro Pro Pro Val Arg Asp Pro Pro Gly Arg Ser Gly Pro Leu Pro
        370             375             380

Pro Pro Pro Pro Val Ser Arg Asn Gly Ser Thr Ser Arg Ala Leu Pro
385             390             395                         400

Ala Thr Pro Gln Leu Pro Ser Arg Ser Gly Val Asp Ser Pro Arg Ser
            405             410                 415

Gly Pro Arg Pro Pro Leu Pro Pro Asp Arg Pro Ser Ala Gly Ala Pro
            420             425             430

Pro Pro Pro Pro Pro Ser Thr Ser Ile Arg Asn Gly Phe Gln Asp Ser
            435             440             445

Pro Cys Glu Asp Glu Trp Glu Ser Arg Phe Tyr Phe His Pro Ile Ser
        450             455             460

Asp Leu Pro Pro Pro Glu Pro Tyr Val Gln Thr Thr Lys Ser Tyr Pro
465             470             475                         480

Ser Lys Leu Ala Arg Asn Glu Ser Arg Ser Gly Ser Asn Arg Arg Glu
            485             490                 495

Arg Gly Gly Pro Pro Leu Pro Pro Ile Pro Arg
            500             505

<210> SEQ ID NO 25
<211> LENGTH: 17
<212> TYPE: PRT
<213> ORGANISM: Artificial Sequence
<220> FEATURE:
<223> OTHER INFORMATION: Translated WIP ORF No.4

<400> SEQUENCE: 25

Ser Leu Ala Ala Leu Leu Tyr Pro Ser Ser Arg Ala Ala Ser Val Gly
1               5                   10                  15

Ile

<210> SEQ ID NO 26
<211> LENGTH: 7
<212> TYPE: PRT
<213> ORGANISM: Artificial Sequence
<220> FEATURE:
<223> OTHER INFORMATION: Translated WIP ORF No.5

<400> SEQUENCE: 26

Glu Leu Asp Thr Leu Pro Pro
1               5
```